United States Patent
Yamajuku et al.

(10) Patent No.: US 10,316,086 B2
(45) Date of Patent: Jun. 11, 2019

(54) ANTI-HUMAN IGβ ANTIBODY

(71) Applicant: Astellas Pharma Inc., Chuo-ku, Tokyo (JP)

(72) Inventors: Daisuke Yamajuku, Tokyo (JP); Mutsumi Seki, Tokyo (JP); Takashi Honda, Tokyo (JP); Satoshi Kubo, Tokyo (JP); Shinji Soga, Tokyo (JP); Akifumi Morinaka, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 196 days.

(21) Appl. No.: 15/501,626

(22) PCT Filed: Aug. 5, 2015

(86) PCT No.: PCT/JP2015/072162
§ 371 (c)(1),
(2) Date: Feb. 3, 2017

(87) PCT Pub. No.: WO2016/021621
PCT Pub. Date: Feb. 11, 2016

(65) Prior Publication Data
US 2017/0226207 A1  Aug. 10, 2017

(30) Foreign Application Priority Data
Aug. 6, 2014  (JP) .................................. 2014-160141

(51) Int. Cl.
| | |
|---|---|
| *C07K 16/00* | (2006.01) |
| *C12P 21/08* | (2006.01) |
| *C07K 16/28* | (2006.01) |
| *A61K 39/395* | (2006.01) |
| *C07K 16/46* | (2006.01) |
| *C12N 5/10* | (2006.01) |
| *C12N 15/02* | (2006.01) |
| *C12N 15/09* | (2006.01) |

(52) U.S. Cl.
CPC ........ *C07K 16/2803* (2013.01); *A61K 39/395* (2013.01); *C07K 16/28* (2013.01); *C07K 16/46* (2013.01); *C12N 5/10* (2013.01); *C12N 15/02* (2013.01); *C12N 15/09* (2013.01); *C07K 2317/24* (2013.01); *C07K 2317/33* (2013.01); *C07K 2317/52* (2013.01); *C07K 2317/56* (2013.01); *C07K 2317/565* (2013.01); *C07K 2317/92* (2013.01)

(58) Field of Classification Search
None
See application file for complete search history.

(56) References Cited

FOREIGN PATENT DOCUMENTS

| | | |
|---|---|---|
| JP | 2013-540696 A | 11/2013 |
| WO | WO 2008/150494 A1 | 12/2008 |
| WO | WO 2009/099728 A1 | 8/2009 |
| WO | WO 2012/018687 A1 | 2/2012 |
| WO | WO 2015/021089 A1 | 2/2015 |

OTHER PUBLICATIONS

Office Action dated Aug. 23, 2018, in EP 15829154.2.
Office Action dated Mar. 8, 2018, in Application No. GC 2015-29837.
International Search Report dated Nov. 2, 2015, in PCT/JP2015/072162.
Chen et al., "Development of human B-lymphocyte targeted bi-specific DART® molecules for the treatment of autoimmune disorders," MacroGenics AAI 2014 Poster MGD010, May 5, 2015, 1 page.
Chu et al., "Inhibition of B cell receptor-mediated activation of primary human B cells by coengagement of CD19 and FcγRIIb with Fc-engineered antibodies," Molecular Immunology, 2008, 45:3926-3933.
Horton et al., "Antibody-Mediated Coengagement of Fcγ RIIb and B Cell Receptor Complex Suppresses Humoral Immunity in Systemic Lupus Erythematosus," The Journal of Immunology, 2011, 186(7):4223-4233.
Veri et al., "Therapeutic Control of B Cell Activation via Recruitment of Fcγ Receptor IIb (CD32B) Inhibitory Function with a Novel Bispecific Antibody Scaffold," Arthritis & Rheumatism, Jul. 2010, 62(7):1933-1943.
Supplementary European Search Report dated Dec. 21, 2017, in EP 15829154.2.

(Continued)

Primary Examiner — Amy E Juedes
(74) Attorney, Agent, or Firm — Foley & Lardner LLP

(57) ABSTRACT

[Problem] Provided is an anti-human Igβ antibody which crosslinks BCR and FcγRIIb and has an immunosuppressive function more enhanced than that of an antibody in the prior art.
[Means for Solution] An anti-human Igβ antibody comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 108 of SEQ ID NO: 2, a light chain variable region comprising CDR1 consisting of the amino acid sequence of amino acid numbers 24 to 38 of SEQ ID NO: 4, CDR2 consisting of the amino acid sequence of amino acid numbers 54 to 60 of SEQ ID NO: 4, and CDR3 consisting of the amino acid sequence of amino acid numbers 93 to 101 of SEQ ID NO: 4, and a heavy chain constant region which is a human Igγ1 constant region having amino acid mutations of S239D, H268D, and L328W.

10 Claims, 3 Drawing Sheets
Specification includes a Sequence Listing.

(56) References Cited

OTHER PUBLICATIONS

Office Action dated Mar. 8, 2018, in Singapore Patent Application No. 11201700885S.
Office Action dated Mar. 22, 2019, in Russian Application No. 2017106743, with English translation.
Office Action dated Apr. 4, 2019, in Singapore Patent Application No. 11201700885S.

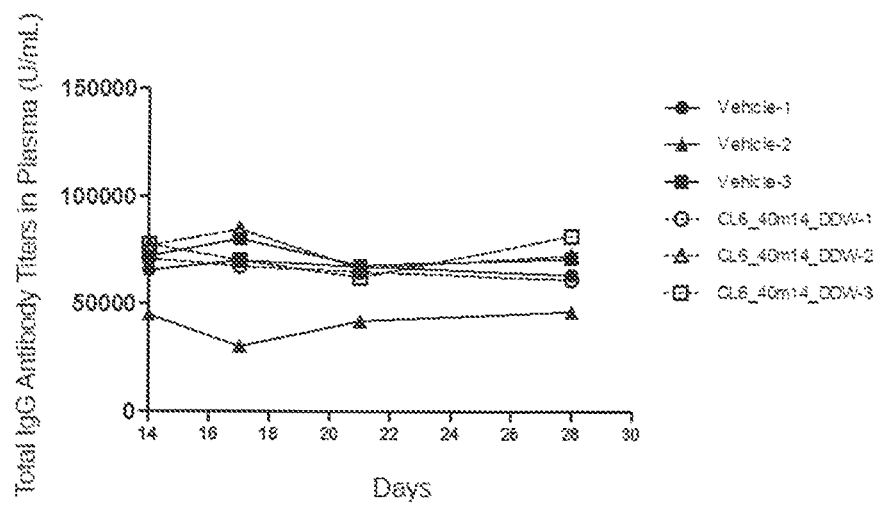

ANTI-HUMAN IGβ ANTIBODY

TECHNICAL FIELD

The present invention relates to a novel anti-human Igβ antibody which is useful as an active ingredient of a pharmaceutical composition.

BACKGROUND ART

A B cell receptor (BCR) is composed of membrane immunoglobulin (mIg) molecules assembled with heterodimers of Igα (CD79A) and Igβ (CD79B). An antigen is bound to the mIg and allow the receptors to aggregate, and an Igα/Igβ subunit transmits a signal to the inside of a B cell (Mol. Immunol., Vol. 41, p. 599-613, 2004).

As for a protein family of an Fcγ receptor (FcγR) which is an Fc receptor against an IgG antibody, FcγRIa (CD64A), FcγRIIa (CD32A), and FcγRIIIa (CD16A) which have immunoactive functions, and FcγRIIb (CD32B) which has immunosuppressive functions have been reported. It has been reported that when BCR and FcγRIIb on B cells are crosslinked through an IgG immune complex, an activity of the B cells is suppressed and thus a proliferation of the B cells and antibody production are suppressed (Nat. Rev. Immunol., Vol. 10, p. 328-343, 2010; Nat. Rev. Immunol., Vol. 8, p. 34-47, 2008; Nat. Rev. Immunol., Vol. 2, p. 580-592, 2002).

It has been reported that control of the activity of B cells through such FcγRIIb is deeply involved in the pathology of autoimmune diseases such as rheumatoid arthritis and systemic lupus erythematosus.

As for the relation to rheumatoid arthritis, it has been reported that in an FcγRIIb knockout mouse, humoral immunity is not appropriately controlled (Nature, Vol. 379, p. 346-349, 1996; J. Immunol., Vol. 163, p. 618-622, 1999) and susceptibility to collagen-induced arthritis is increased (J. Exp. Med., Vol. 189, p. 187-194, 1999). Further, it has been confirmed that expression of FcγRIIb in memory B cells of rheumatoid arthritis patients is decreased (J. Immunol., Vol. 190, p. 6015-6022, 2013).

As for the relation to systemic lupus erythematosus, it has been reported that onset of a systemic lupus erythematosus disease is significantly suppressed in a transgenic mouse in which expression of FcγRIIb is enhanced specifically in B cells (J. Exp. Med., Vol. 205, p. 883-895, 2008). It has been confirmed that in regard to a knockout mouse of FcγRIIb, self-reactive B cells or plasma cells appear and the disease condition of systemic lupus erythematosus develops spontaneously (Immunity, Vol. 13, p. 277-285, 2000; J. Exp. Med., Vol. 207, p. 2767-2778, 2010). Further, a decrease in expression of FcγRIIb in memory B cells of systemic lupus erythematosus patients (J. Exp. Med., Vol. 203, p. 2157-2164, 2006; J. Immunol., Vol. 178, p. 3272-3280, 2007) and relevance between genetic polymorphism in a cell transmembrane region of FcγRIIb and frequency of onsets of systemic lupus erythematosus (Arthritis Rheum., Vol. 46, p. 1242-1254, 2002) have been reported.

Further, suppression of antibody production by controlling an activity of B cells through FcγRIIb is effective for treating an autoimmune disease in which an autoantibody is related to the pathological condition.

Idiopathic thrombocytopenic purpura is an autoimmune disease in which an autoantibody against platelets of a patient causes platelet destruction (Autoimmun. Rev., Vol. 13, p. 577-583, 2014). It has been reported that in an animal to which an antiplatelet antibody is administered, thrombopenia is induced (Br. J. Haematol., Vol. 167, p. 110-120, 2014) and a decrease in an autoantibody are effective for the treatment of idiopathic thrombocytopenic purpura (Ther. Apher. Dial. Vol. 16, p. 311-320, 2012; Lupus, Vol. 22, p. 664-674, 2013).

Therefore, if a monoclonal antibody that crosslinks BCR and FcγRIIb and increases an immunosuppressive function of FcγRIIb can be developed, it is expected that such monoclonal antibody is useful for prevention or treatment of autoimmune diseases such as rheumatoid arthritis, systemic lupus erythematosus, and idiopathic thrombocytopenic purpura.

As an antibody that crosslinks BCR and FcγRIIb, DART which is a bispecific antibody against Igβ and FcγRIIb (Patent Document 1 and Non-Patent Document 1), and anti-CD19 S267E/L328F which has a variable region binding to CD19 which is a part of a BCR complex and an Fc region whose affinity for FcγRIIb is increased (Patent Document 2 and Non-Patent Documents 2 and 3) are reported. Among these, anti-CD19 S267E/L328F is specifically examined, and its inhibitory action with respect to the activity of B cells in which BCR is stimulated and its lowering action of human blood antibody titer concentration in a mouse to which human peripheral blood mononuclear cells (PBMC) are transplanted are confirmed (Patent Document 2 and Non-Patent Documents 2 and 3).

RELATED ART

Patent Document

[Patent Document 1] WO 2012/018687
[Patent Document 2] WO 2008/150494

Non-Patent Document

[Non-Patent Document 1] Arthritis & Rheumatism (US) 2010; 62(7): 1933-1943
[Non-Patent Document 2] Molecular Immunology (US) 2008; 45(15): 3926-3933
[Non-Patent Document 3] The Journal of Immunology (US) 2011; 186(7): 4223-4233

DISCLOSURE OF INVENTION

Problems to be Solved by the Invention

An object of the present invention is to provide an anti-human Igβ antibody which crosslinks BCR and FcγRIIb and has an immunosuppressive function more enhanced than that of an antibody in the prior art.

Means for Solving the Problems

As a result of intensive research on preparation of an anti-human Igβ antibody by the present inventors, a plurality of anti-human Igβ antibodies comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 108 of SEQ ID NO: 2, and a light chain variable region comprising CDR1 consisting of the amino acid sequence of amino acid numbers 24 to 38 of SEQ ID NO: 4, CDR2 consisting of the amino acid sequence of amino acid numbers 54 to 60 of SEQ ID NO: 4, and CDR3 consisting of the amino acid sequence of amino acid numbers 93 to 101 of SEQ ID NO: 4, in which a heavy chain constant region of the antibody is a human Igγ1 constant region having amino acid mutations of S239D, H268D, and L328W were prepared (Examples 1 to 3), and it was found that these antibodies bind to human Igβ on human B cells (Examples 4 and 5) and inhibit activation of the human B cells induced by an anti-IgM antibody (Example 6). As a result, the above-described anti-human Igβ antibody is provided, thereby completing the present invention. Further, it was found that the antibody suppresses the plasma human antibody titer in a human PBMC transfer NOG mouse model (Example 7) and suppresses an antigen-specific antibody without being affected by the total antibody titers in plasma in a monkey TTx antigen sensitization model (Example 8).

That is, the present invention includes the following invention as a material or a method which is medically or industrially applicable.

(1) An anti-human Igβ antibody comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 108 of SEQ ID NO: 2, a light chain variable region comprising CDR1 consisting of the amino acid sequence of amino acid numbers 24 to 38 of SEQ ID NO: 4, CDR2 consisting of the amino acid sequence of amino acid numbers 54 to 60 of SEQ ID NO: 4, and CDR3 consisting of the amino acid sequence of amino acid numbers 93 to 101 of SEQ ID NO: 4, and a heavy chain constant region which is a human Igγ1 constant region having amino acid mutations of S239D, H268D, and L328W.

(2) The anti-human Igβ antibody of (1) above which is a humanized antibody.

(3) The anti-human Igβ antibody of (1) above, selected from the group consisting of the following 1) to 4):

1) an anti-human Igβ antibody comprising a heavy chain variable region consisting of the amino acid sequence of amino acid numbers 1 to 119 of SEQ ID NO: 6, a light chain variable region consisting of the amino acid sequence of amino acid numbers 1 to 112 of SEQ ID NO: 8, and a heavy chain constant region which is a human Igγ1 constant region having amino acid mutations of S239D, H268D, and L328W;

2) an anti-human Igβ antibody comprising a heavy chain variable region consisting of the amino acid sequence of amino acid numbers 1 to 119 of SEQ ID NO: 2, a light chain variable region consisting of the amino acid sequence of amino acid numbers 1 to 112 of SEQ ID NO: 4, and a heavy chain constant region which is a human Igγ1 constant region having amino acid mutations of S239D, H268D, and L328W;

3) an anti-human Igβ antibody comprising a heavy chain variable region consisting of the amino acid sequence of amino acid numbers 1 to 119 of SEQ ID NO: 10, a light chain variable region consisting of the amino acid sequence of amino acid numbers 1 to 112 of SEQ ID NO: 12, and a heavy chain constant region which is a human Igγ1 constant region having amino acid mutations of S239D, H268D, and L328W; and 4) an anti-human Igβ antibody which is derived from posttranslational modification of the anti-human Igβ antibody of any one of (1) to (3) above.

(4) The anti-human Igβ antibody of (3) above, comprising a heavy chain variable region consisting of the amino acid sequence of amino acid numbers 1 to 119 of SEQ ID NO: 6, a light chain variable region consisting of the amino acid sequence of amino acid numbers 1 to 112 of SEQ ID NO: 8, and a heavy chain constant region which is a human Igγ1 constant region having amino acid mutations of S239D, H268D, and L328W.

(5) The anti-human Igβ antibody of (3) above, comprising a heavy chain variable region consisting of the amino acid sequence of amino acid numbers 1 to 119 of SEQ ID NO: 2, a light chain variable region consisting of the amino acid sequence of amino acid numbers 1 to 112 of SEQ ID NO: 4, and a heavy chain constant region which is a human Igγ1 constant region having amino acid mutations of S239D, H268D, and L328W.

(6) The anti-human Igβ antibody of (3) above, comprising a heavy chain variable region consisting of the amino acid sequence of amino acid numbers 1 to 119 of SEQ ID NO: 10, a light chain variable region consisting of the amino acid sequence of amino acid numbers 1 to 112 of SEQ ID NO: 12, and a heavy chain constant region which is a human Igγ1 constant region having amino acid mutations of S239D, H268D, and L328W.

(7) An anti-human Igβ antibody which is derived from posttranslational modification of the anti-human Igβ antibody of any one of (4) to (6) above.

(8) The anti-human Igβ antibody of (3) or (7) above, wherein the posttranslational modification is pyroglutamylation at the N terminal of the heavy chain variable region and/or deletion of lysine at the C terminal of the heavy chain.

(9) The anti-human Igβ antibody of any one of (1) to (8) above, comprising a light chain constant region which is a human Igκ constant region.

(10) The anti-human Igβ antibody of (1) above, comprising a heavy chain consisting of the amino acid sequence shown by SEQ ID NO: 6 and a light chain consisting of the amino acid sequence shown by SEQ ID NO: 8.

(11) The anti-human Igβ antibody of (1), comprising a heavy chain consisting of the amino acid sequence shown by SEQ ID NO: 2 and a light chain consisting of the amino acid sequence shown by SEQ ID NO: 4.

(12) The anti-human Igβ antibody of (1) above, comprising a heavy chain consisting of the amino acid sequence shown by SEQ ID NO: 10 and a light chain consisting of the amino acid sequence shown by SEQ ID NO: 12.

(13) An anti-human Igβ antibody which is derived from posttranslational modification of the anti-human Igβ antibody of any one of (10) to (12) above.

(14) The anti-human Igβ antibody of (13) above, wherein the posttranslational modification is pyroglutamylation at the N terminal of the heavy chain variable region and/or deletion of lysine at the C terminal of the heavy chain.

(15) The anti-human Igβ antibody of (13) above, comprising a heavy chain consisting of the amino acid sequence of amino acid numbers of 1 to 448 of SEQ ID NO: 6 in which glutamine of amino acid number 1 is modified to pyroglutamic acid and a light chain consisting of the amino acid sequence shown by SEQ ID NO:8.

(16) The anti-human Igβ antibody of (13) above, comprising a heavy chain consisting of the amino acid sequence of amino acid numbers 1 to 448 of SEQ ID NO:2 and a light chain consisting of the amino acid sequence shown by SEQ ID NO:4.

(17) The anti-human Igβ antibody of (13) above, comprising a heavy chain consisting of the amino acid sequence of amino acid numbers 1 to 448 of SEQ ID NO:10 and a light chain consisting of the amino acid sequence shown by SEQ ID NO:12.

(18) A polynucleotide comprising a base sequence encoding the heavy chain of the anti-human Igβ antibody of any one of (1) to (6) above.

(19) A polynucleotide comprising a base sequence encoding the light chain of the anti-human Igβ antibody of any one of (1) to (6) above.

(20) An expression vector comprising the polynucleotide of (18) and/or (19) above.

(21) A host cell transformed with the expression vector of (20) above, selected from the group consisting of the following (a) to (d):

(a) a host cell transformed with an expression vector comprising a polynucleotide comprising a base sequence encoding the heavy chain of the anti-human Igβ antibody of any one of (1) to (6) above and a polynucleotide comprising a base sequence encoding the light chain of the antibody;

(b) a host cell transformed with an expression vector comprising a polynucleotide comprising a base sequence encoding the heavy chain of the anti-human Igβ antibody of any one of (1) to (6) above and an expression vector comprising a polynucleotide comprising a base sequence encoding the light chain of the antibody;

(c) a host cell transformed with an expression vector comprising a polynucleotide comprising a base sequence encoding the heavy chain of the anti-human Igβ antibody of any one of (1) to (6) above; and (d) a host cell transformed with an expression vector comprising a polynucleotide comprising a base sequence encoding the light chain of the anti-human Igβ antibody of any one of (1) to (6) above.

(22) A host cell transformed with the expression vector of (20) above, selected from the group consisting of the following (a) to (d):

(a) a host cell transformed with an expression vector comprising a polynucleotide comprising a base sequence encoding the heavy chain of the anti-human Igβ antibody of any one of (10) to (13) above and a polynucleotide comprising a base sequence encoding the light chain of the antibody;

(b) a host cell transformed with an expression vector comprising a polynucleotide comprising a base sequence encoding the heavy chain of the anti-human Igβ antibody of any one of (10) to (13) above and an expression vector comprising a polynucleotide comprising a base sequence encoding the light chain of the antibody;

(c) a host cell transformed with an expression vector comprising a polynucleotide comprising a base sequence encoding the heavy chain of the anti-human Igβ antibody of any one of (10) to (13) above; and (d) a host cell transformed with an expression vector comprising a polynucleotide comprising a base sequence encoding the light chain of the anti-human Igβ antibody of any one of (10) to (13) above.

(23) A method for producing an anti-human Igβ antibody comprising culturing host cell(s) selected from the group consisting of the following (a) to (c) to express the anti-human Igβ antibody:

(a) a host cell transformed with an expression vector comprising a polynucleotide comprising a base sequence encoding the heavy chain of the anti-human Igβ antibody of any one of (1) to (6) above and a polynucleotide comprising a base sequence encoding the light chain of the antibody;

(b) a host cell transformed with an expression vector comprising a polynucleotide comprising a base sequence encoding the heavy chain of the anti-human Igβ antibody of any one of (1) to (6) above and an expression vector comprising a polynucleotide comprising a base sequence encoding the light chain of the antibody; and (c) a host cell transformed with an expression vector comprising a polynucleotide comprising a base sequence encoding the heavy chain of the anti-human Igβ antibody of any one of (1) to (6) above and a host cell transformed with an expression vector comprising a polynucleotide comprising a base sequence encoding the light chain of the antibody.

(24) A method for producing an anti-human Igβ antibody comprising culturing host cell(s) selected from the group consisting of the following (a) to (c) to express the anti-human Igβ antibody:

(a) a host cell transformed with an expression vector comprising a polynucleotide comprising a base sequence encoding the heavy chain of the anti-human Igβ antibody of any one of (10) to (13) above and a polynucleotide comprising a base sequence encoding the light chain of the antibody;

(b) a host cell transformed with an expression vector comprising a polynucleotide comprising a base sequence encoding the heavy chain of the anti-human Igβ antibody of any one of (10) to (13) above and an expression vector comprising a polynucleotide comprising a base sequence encoding the light chain of the antibody; and (c) a host cell transformed with an expression vector comprising a polynucleotide comprising a base sequence encoding the heavy chain of the anti-human Igβ antibody of any one of (10) to (13) above and a host cell transformed with an expression vector comprising a polynucleotide comprising a base sequence encoding the light chain of the antibody.

(25) An anti-human Igβ antibody which is produced by the method of (23) above.

(26) An anti-human Igβ antibody which is produced by the method of (24) above.

(27) A pharmaceutical composition comprising the anti-human Igβ antibody of any one of (1) to (17), (25), and (26) above and a pharmaceutically acceptable excipient.

(28) A pharmaceutical composition comprising the anti-human Igβ antibody of (10) above, the anti-human Igβ antibody of (15) above, and a pharmaceutically acceptable excipient.

(29) The pharmaceutical composition of (27) or (28) above, which is a pharmaceutical composition for preventing or treating an autoimmune disease.

(30) The pharmaceutical composition of (29) above, wherein the autoimmune disease is systemic lupus erythematosus, rheumatoid arthritis, or idiopathic thrombocytopenic purpura.

(31) A method for preventing or treating an autoimmune disease, comprising administrating a therapeutically effective amount of the anti-human Igβ antibody of any one of (1) to (17), (25), and (26) above.

(32) The method of (1) to (17), (25), and (26) above, wherein the autoimmune disease is systemic lupus erythematosus, rheumatoid arthritis, or idiopathic thrombocytopenic purpura.

(33) The anti-human Igβ antibody of any one of (1) to (17), (25), and (26) above for use in preventing or treating an autoimmune disease.

(34) The anti-human Igβ antibody of (33) above, wherein the autoimmune disease is systemic lupus erythematosus, rheumatoid arthritis, or idiopathic thrombocytopenic purpura.

(35) Use of the anti-human Igβ antibody of any one of (1) to (17), (25), and (26) above for manufacture of a pharmaceutical composition for preventing or treating an autoimmune disease.

(36) The use of (35) above, wherein the autoimmune disease is systemic lupus erythematosus, rheumatoid arthritis, or idiopathic thrombocytopenic purpura.

Effects of the Invention

An anti-human Igβ of the present invention has an excellent immunosuppressive action by means of inhibiting activation of B cells and can be used as an agent for preventing or treating of autoimmune diseases such as systemic lupus erythematosus, rheumatoid arthritis, and idiopathic thrombocytopenic purpura.

BRIEF DESCRIPTION OF THE DRAWINGS

FIG. 7 shows an action of the humanized anti-Igβ antibody against total IgG antibody titer in plasma of the monkey immunized by adsorbed tetanus toxoid. The vertical axis indicates the total IgG antibody titer in plasma (U/mL) and the horizontal axis indicates the time (day) from immunizing adsorbed tetanus toxoid to a monkey.

EMBODIMENTS FOR CARRYING OUT THE INVENTION

Figure 1:
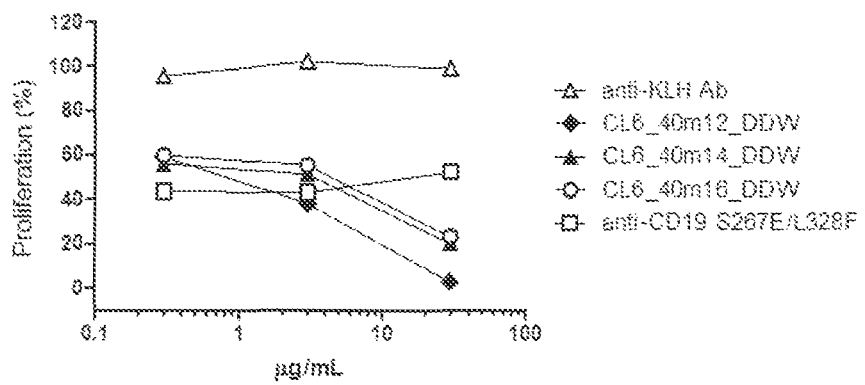
FIG. 1 shows an inhibitory effect of a humanized anti-Igβ antibody against anti-IgM antibody-induced cell proliferation in human B cells. The vertical axis indicates a rate of proliferation of B cells and the horizontal axis indicates added antibody concentration (μg/mL).

Hereinafter, the present invention will be described in detail.

There are five classes of IgG, IgM, IgA, IgD, and IgE in an antibody. The basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, Igδ, and Igε corresponding to IgG, IgM, IgA, IgD, and IgE, respectively. Further, four subclasses of IgG1, IgG2, IgG3, and IgG4 are present in IgG and the heavy chains respectively corresponding thereto are referred to as Igγ1, Igγ2, Igγ3, and Igγ4. Light chain usually consists of a polypeptide chain comprising 220 amino acids, two types of which, type L and type K are known, and are referred to as Igδ and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain. The respective antibody molecules typically consist of two identical light chains and two identical heavy chains.

With regard to intrachain S—S bonds, four of the S—S bonds are present in the heavy chain (five in μ and ε chains) and two of them are present in the light chain; one loop is formed per 100 to 110 amino acid residues, and this steric structure is similar among the loops and are referred to as a structural unit or a domain. The domain located at the amino terminal side (N terminal side) in both of the heavy chain and the light chain, whose amino acid sequence is not constant even in a case of a sample from the same class (sub class) of the same kind of animal is referred to as a variable region, and respective domains are referred to as a heavy chain variable region and a light chain variable region. The amino acid sequence of the carboxy terminal side (C terminal side) from the variable region is nearly constant in each class or subclass and is referred to as a constant region.

An antigenic binding site of an antibody is configured of the heavy chain variable region and the light chain variable region, and the binding specificity depends on the amino acid sequence of this site. On the other hand, biological activities such as binding to complements and various cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

<Anti-Human Igβ Antibody of the Present Invention>

The anti-human Igβ antibody of the present invention includes an anti-human Igβ antibody having the following characteristics.

An anti-human Igβ antibody comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 108 of SEQ ID NO: 2, a light chain variable region comprising CDR1 consisting of the amino acid sequence of amino acid numbers 24 to 38 of SEQ ID NO: 4, CDR2 consisting of the amino acid sequence of amino acid numbers 54 to 60 of SEQ ID NO: 4, and CDR3 consisting of the amino acid sequence of amino acid numbers 93 to 101 of SEQ ID NO: 4, and a heavy chain constant region which is a human Igγ1 constant region having amino acid mutations of S239D, H268D, and L328W.

In one embodiment, the anti-human Igβ antibody of the present invention is a humanized antibody. The "humanized antibody" in the present specification means an antibody in a form comprising CDRs derived from a mouse antibody and other antibody portions derived from a human antibody. A method for preparing a humanized antibody is a known in the art and can be prepared with reference to U.S. Pat. Nos. 5,225,539, 6,180,370, and the like.

In one embodiment, the anti-human Igβ antibody of the present invention is an anti-human Igβ antibody described in any one of the following 1) to 3):

1) an anti-human Igβ antibody comprising a heavy chain variable region consisting of the amino acid sequence of amino acid numbers 1 to 119 of SEQ ID NO: 2, a light chain variable region consisting of the amino acid sequence of amino acid numbers 1 to 112 of SEQ ID NO: 4, and a heavy chain constant region which is a human Igγ1 constant region having amino acid mutations of S239D, H268D, and L328W;

2) an anti-human Igβ antibody comprising a heavy chain variable region consisting of the amino acid sequence of amino acid numbers 1 to 119 of SEQ ID NO: 6, a light chain variable region consisting of the amino acid sequence of amino acid numbers 1 to 112 of SEQ ID NO: 8, and a heavy chain constant region which is a human Igγ1 constant region having amino acid mutations of S239D, H268D, and L328W; and 3) an anti-human Igβ antibody comprising a heavy chain variable region consisting of the amino acid sequence of amino acid numbers 1 to 119 of SEQ ID NO: 10, a light chain variable region consisting of the amino acid sequence of amino acid numbers 1 to 112 of SEQ ID NO: 12, and a heavy chain constant region which is a human Igγ1 constant region having amino acid mutations of S239D, H268D, and L328W.

The number of residue regarding introduction of amino acid mutations in an antibody constant region used in the present specification follows the EU index (Kabat et al. 1991, Sequences of Proteins of Immunological Interest, 5$^{th}$ Ed., United States Public Health Service, National Institute of Health, Bethesda). S239D is replacement of serine at 239$^{th}$ position of the amino acid according to the EU index of Kabat et al. in the human Igγ1 constant region with aspartic acid. H268D is replacement of histidine at 268$^{th}$ position of the amino acid according to the EU index of Kabat et al. in the human Igγ1 constant region with aspartic acid. L328W is replacement of leucine at 328$^{th}$ position of the amino acid according to the EU index of Kabat et al. in the human Igγ1 constant region with triptophan. Examples of the human Igγ1 constant region having amino acid mutations of S239D, H268D, and L328W include a human Igγ1 constant region consisting of the amino acid sequence of amino acid numbers 120 to 449 of SEQ ID NO: 2.

As the light chain constant region of the anti-human Igβ antibody of the present invention, any one of constant region of Igλ and Igκ can be selected, but a human Igκ constant region is preferable. Examples of the human Igκ constant region include a human Igκ constant region consisting of amino acid sequence of amino acid numbers 113 to 218 of SEQ ID NO: 4.

In one embodiment, the anti-human Igβ antibody of the present invention is an anti-human Igβ antibody selected from any one of the following i) to iii):

i) an anti-human Igβ antibody comprising a heavy chain consisting of the amino acid sequence shown by SEQ ID NO: 2 and a light chain consisting of the amino acid sequence shown by SEQ ID NO: 4;

ii) an anti-human Igβ antibody comprising a heavy chain consisting of the amino acid sequence shown by SEQ ID NO: 6 and a light chain consisting of the amino acid sequence shown by SEQ ID NO: 8; and iii) an anti-human Igβ antibody comprising a heavy chain consisting of the amino acid sequence shown by SEQ ID NO: 10 and a light chain consisting of the amino acid sequence shown by SEQ ID NO: 12.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (Journal of Pharmaceutical Sciences, Vol. 97, p. 2426-2447, 2008).

The anti-human Igβ antibody of the present invention includes an anti-human Igβ antibody which has undergone posttranslational modification. Examples of the anti-human Igβ antibody of the present invention which undergoes posttranslational modification include anti-human Igβ antibodies which have undergone pyroglutamylation at the N terminal of the heavy chain variable region and/or deletion of lysine at the C terminal of the heavy chain. It is known in the field that such posttranslational modification due to pyroglutamylation at the N terminal and deletion of lysine at the C terminal does not have any influence on the activity of the antibody (Analytical Biochemistry, Vol. 348, p. 24-39, 2006).

For example, the anti-human Igβ antibodies of the present invention include an anti-human Igβ antibody described in any one of the following 1) to 3):

1) an anti-human Igβ antibody comprising a heavy chain consisting of the amino acid sequence of SEQ ID NO: 2 in which glutamic acid of amino acid number 1 is modified to pyroglutamic acid and/or lysine of amino acid number 449 is deleted and a light chain consisting of the amino acid sequence shown by SEQ ID NO: 4;

2) an anti-human Igβ antibody comprising a heavy chain consisting of the amino acid sequence of SEQ ID NO: 6 in which glutamic acid of amino acid number 1 is modified to pyroglutamic acid and/or lysine of amino acid number 449 is deleted and a light chain consisting of the amino acid sequence shown by SEQ ID NO: 8; and 3) an anti-human Igβ antibody comprising a heavy chain consisting of the amino acid sequence of SEQ ID NO: 10 in which glutamic acid of amino acid number 1 is modified to pyroglutamic acid and/or lysine of amino acid number 449 is deleted and a light chain consisting of the amino acid sequence shown by SEQ ID NO: 12.

In one embodiment, the anti-human Igβ antibody of the present invention is an anti-human Igβ antibody selected from any one of the following i) to iii):

i) an anti-human Igβ antibody comprising a heavy chain consisting of the amino acid sequence of amino acid numbers of 1 to 448 of SEQ ID NO: 2 and a light chain consisting of the amino acid sequence shown by SEQ ID NO: 4;

ii) an anti-human Igβ antibody comprising a heavy chain consisting of the amino acid sequence of amino acid numbers 1 to 448 of SEQ ID NO: 6 in which glutamine of amino acid number 1 is modified to pyroglutamic acid and a light chain consisting of the amino acid sequence shown by SEQ ID NO: 8; and iii) an anti-human Igβ antibody comprising a heavy chain consisting of the amino acid sequence of amino acid numbers 1 to 448 of SEQ ID NO: 10 and a light chain consisting of the amino acid sequence shown by SEQ ID NO: 12.

Any person skilled in the art can prepare a fused form of an antibody and another peptide or protein and can also prepare a modified form to which a modifying agent binds on the basis of the present invention, and the antibody of the present invention includes the antibody in these forms. Other peptides or proteins used for the fusion is not particularly limited as long as the binding activity of the antibody is not decreased, and examples thereof include human serum albumin, various tag peptides, artificial helix motif peptide, maltose-binding proteins, glutathione S transferase, various toxins, other peptides or proteins capable of promoting multimerization, and the like. The modifying agent used for the modification is not particularly limited as long as the binding activity of the antibody is not decreased, and examples thereof include polyethylene glycol, sugar chains, phospholipids, liposomes, low-molecular compounds, and the like.

The "anti-human Igβ antibody" in the present specification means an antibody binding to a human Igβ. Whether the "anti-human Igβ antibody" binds to a human Igβ is confirmed by using a known binding activity measurement method. Examples of the binding activity measurement method include a method of Enzyme-Linked ImmunoSorbent Assay (ELISA) and the like. In a case of using the ELISA, for example, human Igβ-Flag protein (for example, encoded by the base sequence of SEQ ID NO: 13) is solidified on the ELISA Plate and a test antibody is added thereto to be reacted. After the reaction, a secondary antibody such as an anti-IgG antibody, labeled with an enzyme such as horseradish peroxidase (HRP) or the like, is reacted, and washed off, and then it is possible to confirm whether the test antibody binds to the human Igβ by identifying binding of the secondary antibody through activity measurement using a reagent detecting the activity (for example, in a case of HRP labeling, BM-Chemiluminescence ELISA Substrate (POD) (Roche Diagnostics Inc.)). As a specific measurement method, the method described in Example 4 below can be used.

The anti-human Igβ antibody of the present invention includes, in addition to binding to human Igβ, an antibody binding to Igβ derived from other animals (for example, monkey Igβ), as long as the antibody binds to human Igβ.

As a method for evaluating the activity of the anti-human Igβ antibody of the present invention, the binding activity on human B cells or the activity of inhibiting activation of the human B cells induced by BCR stimulation may be evaluated. As the methods of evaluating such activity, the methods described in Examples 5 and 6 below can be used. Preferably, the anti-human Igβ antibody of the present invention has an activity of binding to human Igβ and inhibiting activation of human B cells induced by BCR stimulation.

The anti-human Igβ antibody of the present invention can be easily prepared by a person skilled in the art using a known method in the field, based on sequence information on the heavy chain and the light chain of the antibody of the present invention, which is disclosed in the present specification. The anti-human Igβ antibody of the present invention is not particularly limited, but can be produced according to the method described in the section of <Method of producing anti-human Igβ antibody of the present invention, and anti-human Igβ antibody produced by the method> described below.

The anti-human Igβ antibody of the present invention is further purified as needed, formulated according to a conventional method, and may be used for the prevention or the treatment of autoimmune diseases such as systemic lupus erythematosus, rheumatoid arthritis, idiopathic thrombocytopenic purpura, myasthenia gravis, Grave's disease, optic neuromyelitis, autoimmune hemolytic anemia, pemphigus, antiphospholipid antibody syndrome, ANCA associated vasculitis, Sjogren's syndrome, Hashimoto's disease, chronic inflammatory demyelinating polyneuropathy, or chronic fatigue syndrome.

<Polynucleotide of the Present Invention>

The polynucleotide of the present invention includes a polynucleotide comprising a base sequence encoding the heavy chain of the anti-human Igβ antibody of the present invention and a polynucleotide comprising a base sequence encoding the light chain of the anti-human Igβ antibody of the present invention.

In one embodiment, the polynucleotide comprising a base sequence encoding the heavy chain of the anti-human Igβ antibody of the present invention is a polynucleotide comprising a base sequence encoding the heavy chain consisting of the amino acid sequence shown by SEQ ID NO: 2, a polynucleotide comprising a base sequence encoding the heavy chain consisting of the amino acid sequence shown by SEQ ID NO: 6, or a polynucleotide comprising a base sequence encoding the heavy chain consisting of the amino acid sequence shown by SEQ ID NO: 10.

Examples of the polynucleotide comprising a base sequence encoding the heavy chain consisting of the amino acid sequence shown by SEQ ID NO: 2 include a polynucleotide comprising the base sequence shown by SEQ ID NO: 1 or 15. Examples of the polynucleotide comprising a base sequence encoding the heavy chain consisting of the amino acid sequence shown by SEQ ID NO: 6 include a polynucleotide comprising the base sequence shown by SEQ ID NO: 5. Examples of the polynucleotide comprising a base sequence encoding the heavy chain consisting of the amino acid sequence shown by SEQ ID NO: 10 include a polynucleotide comprising the base sequence shown by SEQ ID NO: 9.

In one embodiment, the polynucleotide comprising a base sequence encoding the light chain of the anti-human Igβ antibody of the present invention is a polynucleotide comprising a base sequence encoding the light chain consisting of the amino acid sequence shown by SEQ ID NO: 4, a polynucleotide comprising a base sequence encoding the light chain consisting of the amino acid sequence shown by SEQ ID NO: 8, or a polynucleotide comprising a base sequence encoding the light chain consisting of the amino acid sequence shown by SEQ ID NO: 12.

Examples of the polynucleotide comprising a base sequence encoding the light chain consisting of the amino acid sequence shown by SEQ ID NO: 4 include a polynucleotide comprising the base sequence shown by SEQ ID NO: 3. Examples of the polynucleotide comprising a base sequence encoding the light chain consisting of the amino acid sequence shown by SEQ ID NO: 8 include a polynucleotide comprising the base sequence shown by SEQ ID NO: 7. Examples of the polynucleotide comprising a base sequence encoding the light chain consisting of the amino acid sequence shown by SEQ ID NO: 12 include a polynucleotide comprising the base sequence shown by SEQ ID NO: 11.

The polynucleotide of the present invention can be easily prepared by a person skilled in the art using a known method in the field based on the base sequence. For example, the polynucleotide of the present invention can be synthesized using a known gene synthesis method in the field. As the gene synthesis method, various methods such as a synthesis method of antibody genes described in WO90/07861 known by a person skilled in the art can be used.

<Expression Vector of the Present Invention>

An expression vector of the present invention includes an expression vector comprising a polynucleotide comprising a base sequence encoding the heavy chain of the anti-human Igβ antibody of the present invention, an expression vector comprising a polynucleotide comprising a base sequence encoding the light chain of the anti-human Igβ antibody of the present invention, and an expression vector comprising a polynucleotide comprising a base sequence encoding the heavy chain of the anti-human Igβ antibody of the present invention and a polynucleotide comprising a base sequence encoding the light chain of the antibody.

The expression vector used to express the polynucleotide of the present invention are not particularly limited as long as a polynucleotide comprising the base sequence encoding the heavy chain of the anti-human Igβ antibody of the present invention and/or a polynucleotide comprising the base sequence encoding the light chain of the anti-human Igβ antibody of the present invention can be expressed in various host cells of eukaryotic cells (for example, animal cells, insect cells, plant cells, and yeast) and/or prokaryotic cells (for example, *Escherichia coli*), and the polypeptides encoded by these can be produced. Examples of the expression vector include plasmid vectors, viral vectors (for example, adenovirus or retrovirus), and the like. Preferably pEE6.4 or pEE02.4 (Lonza Biologics, Inc.) can be used.

The expression vector of the present invention may include a promoter that is operably linked to the polynucleotide of the present invention. Examples of the promoter for expressing the polynucleotide of the invention with animal cells include a virus-derived promoter such as CMV, RSV, or SV40, an actin promoter, an EF (elongation factor) 1α promoter, and a heat shock promoter. Examples of promoters for expressing the polynucleotide of the invention by bacteria (for example, *Escherichia*) include a trp promoter, a lac promoter, XPL promoter, and tac promoter. Further, examples of promoters for expressing the polynucleotide of the invention by yeast include a GAL 1 promoter, a GAL 10 promoter, a PH05 promoter, a PGK promoter, a GAP promoter, and an ADH promoter.

In the case of using an animal cell, an insect cell, or yeast as the host cell, the expression vector of the present invention may comprise initiation codon and termination codon. In this case, the expression vector of the present invention may comprise an enhancer sequence, an untranslated region on the 5' side and the 3' side of genes encoding the antibody of the present invention or the heavy chain or the light chain, a secretory signal sequence, a splicing junction, a polyadenylation site, or a replicable unit. When *Escherichia coli* is used as the host cell, the expression vector of the present invention may comprise an initiation codon, a termination codon, a terminator region, and a replicable unit. In this case, the expression vector of the present invention may comprise a selection marker (for example, tetracycline resistant genes, ampicillin resistant genes, kanamycin resistant genes, neomycin resistant genes, or dihydrofolate reductase genes) which is generally used according to the necessity.

<Transformed Host Cell of the Present Invention>

The transformed host cell of the present invention includes a host cell transformed with the expression vector of the present invention, which is selected from the group consisting of the following (a) to (d):

(a) a host cell transformed with an expression vector comprising a polynucleotide comprising a base sequence encoding the heavy chain of the anti-human Igβ antibody of the present invention and a polynucleotide comprising a base sequence encoding the light chain of the antibody;

(b) a host cell transformed with an expression vector comprising a polynucleotide comprising a base sequence encoding the heavy chain of the anti-human Igβ antibody of the present invention and an expression vector comprising a polynucleotide comprising a base sequence encoding the light chain of the antibody;

(c) a host cell transformed with an expression vector comprising a polynucleotide comprising a base sequence encoding the heavy chain of the anti-human Igβ antibody of the present invention; and (d) a host cell transformed with an expression vector comprising a polynucleotide comprising a base sequence encoding the light chain of the anti-human Igβ antibody of the present invention.

Examples of the preferred transformed host cell of the present invention include a host cell transformed with an expression vector comprising a polynucleotide comprising a base sequence encoding the heavy chain of the anti-human Igβ antibody of the present invention and a polynucleotide comprising a base sequence encoding the light chain of the antibody, and a host cell transformed with an expression vector comprising a polynucleotide comprising a base sequence encoding the heavy chain of the anti-human Igβ antibody of the present invention and an expression vector comprising a polynucleotide comprising a base sequence encoding the light chain of the antibody.

The transformed host cell is not particularly limited as long as the host cell is appropriate for the expression vector being used, transformed with the expression vector, and can express the antibody. Examples of the transformed host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) or the like). Preferably cultured cells such as CHO-K1SV cells, CHO-DG 44 cells, 293 cells, or NS0 cells can be used.

A method of transforming the host cell is not particularly limited, but, for example, a calcium phosphate method or an electroporation method can be used.

<Method of Producing Anti-Human Igβ Antibody of the Present Invention, and Anti-Human Igβ Antibody Produced by the Method>

The method for producing the anti-human Igβ antibody of the present invention include a method for producing an anti-human Igβ antibody by culturing host cell(s) selected from the group consisting of the following (a) to (c) to express the anti-human Igβ antibody:

(a) a host cell transformed with an expression vector comprising a polynucleotide comprising a base sequence encoding the heavy chain of the anti-human Igβ antibody of the present invention and a polynucleotide comprising a base sequence encoding the light chain of the antibody;

(b) a host cell transformed with an expression vector comprising a polynucleotide comprising a base sequence encoding the heavy chain of the anti-human Igβ antibody of the present invention and an expression vector comprising a polynucleotide comprising a base sequence encoding the light chain of the antibody; and (c) a host cell transformed with an expression vector comprising a polynucleotide comprising a base sequence encoding the heavy chain of the anti-human Igβ antibody of the present invention and a host cell transformed with an expression vector comprising a polynucleotide comprising a base sequence encoding the light chain of the antibody.

The method for producing the anti-human Igβ antibody of the present invention is not particularly limited as long as it includes a step of culturing the transformed host cells of the present invention to express the anti-human Igβ antibody. Examples of the preferred host cells used in the method include the preferred transformed host cells of the present invention as described above.

The transformed host cell can be cultured by known methods. Culture conditions, for example, the temperature, pH of culture medium, and the culture time are appropriately selected. In a case where the host cell is an animal cell, examples of the culture medium include MEM culture medium supplemented with approximately 5% to 20% of fetal bovine serum (Science, Vol. 130, p. 432-437, 1959), DMEM culture medium (Virology, Vol. 8, p. 396, 1959), RPMI1640 culture medium (J. Am. Med. Assoc., Vol. 199, p. 519, 1967), and a 199 culture medium (Exp. Biol. Med., Vol. 73, p. 1-8, 1950). The pH of the culture medium is preferably approximately 6 to 8, and the culture is generally carried out at approximately 30° C. to 40° C. for approximately 15 hours to 72 hours while air ventilating and stirring if necessary. In a case where the host cell is an insect cell, as the culture medium, for example, Grace's culture medium (Proc. Natl. Acad. Sci. USA, Vol. 82, p. 8404, 1985) supplemented with fetal bovine serum can be used. The pH of the culture medium is preferably approximately 5 to 8, and the culture is generally carried out at approximately 20° C. to 40° C. for approximately 15 hours to 100 hours while air ventilating and stirring if necessary. In a case where the host cell is *Escherichia coli* or yeast, as the culture medium, for example, liquid culture medium supplemented with a source of nutrients is appropriate. It is preferable that the nutrient culture medium include a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the culture medium is preferably approximately 5 to 8. In a case where the host cell is *Escherichia coli*, preferred examples of the culture medium include LB culture medium and M9 culture medium (Mol. Clo., Cold Spring Harbor Laboratory, Vol. 3, A2.2). The culture is generally carried out at approximately 14° C. to 43° C. for approximately 3 hours to 24 hours while air ventilating and stirring if necessary. In a case where the host cell is yeast, as the culture medium, for example, Burkholder minimal medium (Proc. Natl. Acad, Sci, USA, Vol. 77, p. 4505, 1980) can be used. The culture is generally carried out at approximately 20° C. to 35° C. for approximately 14 hours to 144 hours while air ventilating and stirring if necessary. By carrying out the culture in the above-described manner, it is possible to express the anti-human Igβ antibody of the present invention.

The method of producing the anti-human Igβ antibody of the present invention may include recovering, preferably isolating or purifying the anti-human Igβ antibody from the transformed host cell in addition to culturing the transformed host cell of the present invention to express the anti-human Igβ antibody. Examples of the isolation or purification method include methods using solubility such as salting-out and the solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing phoresis. Preferably, the antibody accumulated in a culture supernatant can be purified by various chromatographies, for example, column chromatography using Protein A column or Protein G column.

The anti-human Igβ antibody of the present invention also includes an anti-human Igβ antibody produced by the method for producing the anti-human Igβ antibody of the present invention.

<Pharmaceutical Composition of the Present Invention>

The pharmaceutical compositions of the present invention include a pharmaceutical composition comprising the anti-human Igβ antibody of the present invention and pharmaceutically acceptable excipients. The pharmaceutical composition of the present invention can be prepared by a method being generally used with excipients, that is, excipients for medicine or carriers for medicine being generally used in the field. Examples of dosage forms of the pharmaceutical compositions include parenteral drug such as an injection drug and a drip infusion drug, and these can be administered by intravenous administration, subcutaneous administration, or the like. In drug preparation, excipients, carriers, and additives in accordance with the dosage forms can be used within the pharmaceutically acceptable range.

The pharmaceutical compositions of the present invention may include plural kinds of anti-human Igβ antibody of the present invention. For example, the present invention includes a pharmaceutical composition comprising an antibody which does not undergo posttranslational modification and an antibody derived from posttranslational modification of the antibody.

In one embodiment, the pharmaceutical composition of the present invention comprises an anti-human Igβ antibody selected from the group consisting of the following (1) to (3) and an anti-human Igβ antibody derived from posttranslational modification of the anti-human Igβ antibody:

(1) an anti-human Igβ antibody comprising a heavy chain variable region consisting of the amino acid sequence of amino acid numbers 1 to 119 of SEQ ID NO: 6, a light chain variable region consisting of the amino acid sequence of amino acid numbers 1 to 112 of SEQ ID NO: 8, and a heavy chain constant region which is a human Igγ1 constant region having amino acid mutations of S239D, H268D, and L328W;

(2) an anti-human Igβ antibody comprising a heavy chain variable region consisting of the amino acid sequence of amino acid numbers 1 to 119 of SEQ ID NO: 2, a light chain variable region consisting of the amino acid sequence of amino acid numbers 1 to 112 of SEQ ID NO: 4, and a heavy chain constant region which is a human Igγ1 constant region having amino acid mutations of S239D, H268D, and L328W; and (3) an anti-human Igβ antibody comprising a heavy chain variable region consisting of the amino acid sequence of amino acid numbers 1 to 119 of SEQ ID NO: 10, a light chain variable region consisting of the amino acid sequence of amino acid numbers 1 to 112 of SEQ ID NO: 12, and a heavy chain constant region which is a human Igγ1 constant region having amino acid mutations of S239D, H268D, and L328W.

The pharmaceutical compositions of the present invention include a pharmaceutical composition comprising an antibody in which lysine at the C terminal of the heavy chain is deleted, an antibody which has undergone post-translational modification to the N terminal, an antibody in which lysine at the C terminal of the heavy chain is deleted and which has undergone post-translation modification to N terminal, and/or an antibody which has lysine at the C terminal of the heavy chain and does not undergo post-translational modification to the N terminal.

In one embodiment, the pharmaceutical composition of the present invention comprising an anti-human Igβ antibody includes a pharmaceutical composition comprising two or more anti-human Igβ antibodies selected from the following (1) to (4):

(1) an anti-human Igβ antibody comprising a heavy chain consisting of the amino acid sequence of amino acid numbers 1 to 448 of SEQ ID NO: 2 and a light chain consisting of the amino acid sequence shown by SEQ ID NO: 4;

(2) an anti-human Igβ antibody comprising a heavy chain consisting of the amino acid sequence of SEQ ID NO: 2 in which glutamic acid of amino acid number 1 is modified to pyroglutamic acid and a light chain consisting of the amino acid sequence shown by SEQ ID NO: 4;

(3) an anti-human Igβ antibody comprising a heavy chain consisting of the amino acid sequence of amino acid numbers 1 to 448 of SEQ ID NO: 2 in which glutamic acid of amino acid number 1 is modified to pyroglutamic acid and a light chain consisting of the amino acid sequence shown by SEQ ID NO: 4; and (4) an anti-human Igβ antibody comprising a heavy chain consisting of the amino acid sequence shown by SEQ ID NO:2 and a light chain consisting of the amino acid sequence shown by SEQ ID NO: 4.

In one embodiment, the pharmaceutical composition of the present invention comprising an anti-human Igβ antibody includes a pharmaceutical composition comprising two or more anti-human Igβ antibodies selected from the following (1) to (4):

(1) an anti-human Igβ antibody comprising a heavy chain consisting of the amino acid sequence of amino acid numbers 1 to 448 of SEQ ID NO: 6 and a light chain consisting of the amino acid sequence shown by SEQ ID NO: 8;

(2) an anti-human Igβ antibody comprising a heavy chain consisting of the amino acid sequence of SEQ ID NO: 6 in which glutamine of amino acid number 1 is modified to pyroglutamic acid and a light chain consisting of the amino acid sequence shown by SEQ ID NO: 8;

(3) an anti-human Igβ antibody comprising a heavy chain consisting of the amino acid sequence of amino acid numbers 1 to 448 of SEQ ID NO: 6 in which glutamine of amino acid number 1 is modified to pyroglutamic acid and a light chain consisting of the amino acid sequence shown by SEQ ID NO: 8; and (4) an anti-human Igβ antibody comprising a heavy chain consisting of the amino acid sequence shown by SEQ ID NO:6 and a light chain consisting of the amino acid sequence shown by SEQ ID NO: 8.

In one embodiment, the pharmaceutical composition of the present invention comprising an anti-human Igβ antibody includes a pharmaceutical composition comprising two or more anti-human Igβ antibodies selected from the following (1) to (4):

(1) an anti-human Igβ antibody comprising a heavy chain consisting of the amino acid sequence of amino acid numbers 1 to 448 of SEQ ID NO: 10 and a light chain consisting of the amino acid sequence shown by SEQ ID NO: 12;

(2) an anti-human Igβ antibody comprising a heavy chain consisting of the amino acid sequence of SEQ ID NO: 10 in which glutamic acid of amino acid number 1 is modified to pyroglutamic acid and a light chain consisting of the amino acid sequence shown by SEQ ID NO: 12;

(3) an anti-human Igβ antibody comprising a heavy chain consisting of the amino acid sequence of amino acid numbers 1 to 448 of SEQ ID NO: 10 in which glutamic acid of amino acid number 1 is modified to pyroglutamic acid and a light chain consisting of the amino acid sequence shown by SEQ ID NO: 12; and (4) an anti-human Igβ antibody comprising a heavy chain consisting of the amino acid sequence shown by SEQ ID NO: 10 and a light chain consisting of the amino acid sequence shown by SEQ ID NO: 12.

Further, in one embodiment, the pharmaceutical composition of the present invention is a pharmaceutical composition described below:

a pharmaceutical composition comprising an anti-human Igβ antibody comprising a heavy chain consisting of the amino acid sequence shown by SEQ ID NO: 6 and a light chain consisting of the amino acid sequence shown by SEQ ID NO: 8, an anti-human Igβ antibody comprising a heavy chain consisting of the amino acid sequence of amino acid numbers 1 to 448 of SEQ ID NO: 6 in which glutamine of amino acid number 1 is modified to pyroglutamic acid and a light chain consisting of the amino acid sequence shown by SEQ ID NO: 8, and a pharmaceutically acceptable excipient.

The addition amount of the anti-human Igβ antibody of the present invention in formulation varies depending on the degree of a patient's symptoms, the age of a patient, a dosage form of the drug to be used, the binding titer of the antibody, or the like, and for example, an addition amount of approximately 0.001 mg/kg to 100 mg/kg can be used.

The pharmaceutical composition of the present invention can be used as an agent for treating autoimmune diseases such as systemic lupus erythematosus, rheumatoid arthritis, idiopathic thrombocytopenic purpura, myasthenia gravis, Grave's disease, optic neuromyelitis, autoimmune hemolytic anemia, pemphigus, antiphospholipid antibody syndrome, ANCA associated vasculitis, Sjogren's syndrome, Hashimoto's disease, chronic inflammatory demyelinating polyneuropathy, chronic fatigue syndrome, or the like.

The present invention includes a pharmaceutical composition for preventing or treating systemic lupus erythematosus, rheumatoid arthritis, or idiopathic thrombocytopenic purpura comprising the anti-human Igβ antibody of the present invention. Further, the present invention includes a method for preventing or treating systemic lupus erythematosus, rheumatoid arthritis, or idiopathic thrombocytopenic purpura comprising administering a therapeutically effective amount of the anti-human Igβ antibody of the present invention. Further, the present invention includes the anti-human Igβ antibody of the present invention for use in preventing or treating systemic lupus erythematosus, rheumatoid arthritis, or idiopathic thrombocytopenic purpura. In addition, the present invention includes use of the anti-human Igβ antibody of the present invention for manufacture of a pharmaceutical composition for preventing or treating systemic lupus erythematosus, rheumatoid arthritis, or idiopathic thrombocytopenic purpura.

The present invention has been described and specific examples referred to for better understanding will be provided, but these are merely examples and the present invention is not limited thereto.

EXAMPLES

With regard to parts using commercially available kits or reagents, the tests are performed according to the attached protocol unless otherwise noted.

Example 1

Acquisition of Human and Monkey Igβ-Flag Proteins

A protein in which a Flag tag binds to human Igβ (human Igβ-Flag protein) and a protein in a Flag tag binds to which monkey Igβ (monkey Igβ-Flag protein) were acquired. A human Igβ-Flag gene (SEQ ID NO: 13) was introduced into a GS vector pEE6.4 (Lonza Biologics, Inc.). A monkey Igβ-Flag gene (SEQ ID NO: 14) was introduced into a GS vector pEE6.4 (Lonza Biologics, Inc.). The respective prepared vectors were gene-transferred to FreeStyle 293 cells (Life Technologies, Inc.) using a FreeStyle MAX Reagent (life Technologies, Inc.). Respective cells were cultured in a serum-free culture system using a FreeStyle 293 Expression medium (Life Technologies, Inc.) for 1 week and culture supernatants respectively containing human Igβ-Flag protein and monkey Igβ-Flag protein were acquired. The proteins were purified using an anti-Flag M2 antibody affinity gel (SIGMA-ALDRICH Corporation) from the acquired culture supernatants and then used for the following test.

Example 2

Acquisition of Anti-human Igβ Antibody

In order to acquire an anti-human Igβ antibody, the human Igβ-Flag protein and the monkey Igβ-Flag protein acquired in Example 1 were injected to a C3H/HeJJmsSlc-lpr/lpr mouse (Japan SLC, Inc.) together with an adjuvant for causing an immune reaction to perform immunization. The mouse was immunized several times and final immunization was performed. According to the conventional method, a spleen and a lymph node of the immunized mouse was extracted, and lymphocytes were collected and cell-fused with mouse myeloma cells SP2/0 (ATCC CRL-1581), thereby preparing a hybridoma. A limiting dilution sample of the hybridoma was prepared and the hybridoma was monocloned. Respective clones were expanded and cultured, the culture medium was changed to Hybridoma SFM (Life Technologies, Inc.), which is a serum-free culture medium, and then the clones were cultured for 3 to 5 days. An antibody was purified using an antibody purifying kit (Protein G Purification kit; Proteus, Inc.) from the obtained culture supernatant.

In regard to the antibodies obtained from respective clones, the binding activity on human and monkey Igβ-Flag proteins and the binding activity on human and monkey B cells were evaluated. As a result, it was found that an antibody referred to as CL6_40 was bound to both of the human and monkey Igβ-Flag proteins and had a high binding activity with respect to both of the human and monkey B cells. In regard to CL6_40, genes encoding a heavy chain and a light chain from Hybridoma were cloned and sequence determination was performed.

Example 3

Preparation of Humanized Antibody

CDRs of the heavy chain and the light chain of CL6_40 were transplanted to other human antibodies, and a plurality of genes of heavy chains and light chains of humanized antibodies were prepared. An expression vector comprising both genes of a heavy chain and a light chain of respective humanized antibodies was constructed using a GS vector (Lonza Biologics, Inc.). Specifically, genes encoding signal sequences (N. Whittle et al., Protein Eng., Vol. 1, p. 499-505, 1987) and the constant region gene of human Igγ1 (consisting of the base sequence of base numbers 358 to 1350 of SEQ ID NO: 1) having amino acid mutations of S239D, H268D, and L328W were respectively ligated to the 5' side and the 3' side of the heavy chain variable region genes of respective humanized antibodies, and then the heavy chain genes were inserted into a GS vector pEE6.4. Further, genes encoding signal sequences (N. Whittle et al., mentioned above) and the constant region genes of a human κ chain (consisting of the base sequence of base numbers 337 to 657 of SEQ ID NO: 3) were respectively ligated to the 5' side and the 3' side of the light chain variable region genes of the respective humanized antibodies, and then the light chain genes were inserted into a GS vector pEE12.4.

The base sequence of the heavy chain of the prepared humanized antibody CL6_40m12_DDW is shown by SEQ ID NOS: 1 and 15, the amino acid sequence encoded by the base sequence is shown by SEQ ID NO: 2, the base sequence of the light chain of the antibody is shown by SEQ ID NO: 3, and the amino acid sequence encoded by the base sequence is shown by SEQ ID NO: 4. The heavy chain variable region shown by SEQ ID NO: 2 consists of the amino acid sequence of amino acid numbers 1 to 119 of SEQ ID NO: 2, and the CDR1, CDR2, and CDR3 of the heavy chain each consist of the amino acid sequence of amino acid numbers 31 to 35, 50 to 65, and 98 to 108 of SEQ ID NO: 2. The light chain variable region shown by SEQ ID NO: 4 consists of the amino acid sequence of amino acid numbers 1 to 112 of SEQ ID NO: 4, and the CDR1, CDR2, and CDR3 of the light chain each consist of the amino acid sequence of amino acid numbers 24 to 38, 54 to 60, and 93 to 101 of SEQ ID NO: 4.

The base sequence of the heavy chain of the prepared humanized antibody CL6_40m14_DDW is shown by SEQ ID NO: 5, the amino acid sequence encoded by the base sequence is shown by SEQ ID NO: 6, the base sequence of the light chain of the antibody is shown by SEQ ID NO: 7, and the amino acid sequence encoded by the base sequence is shown by SEQ ID NO: 8. The variable region of the heavy chain shown by SEQ ID NO: 6 consists of the amino acid sequence of amino acid numbers 1 to 119 of SEQ ID NO: 6, and the CDR1, CDR2, and CDR3 of the heavy chain respectively consist of the amino acid sequence of amino acid numbers 31 to 35, 50 to 65, and 98 to 108 of SEQ ID NO: 6. The variable region of the light chain shown by SEQ ID NO: 8 consists of the amino acid sequence of amino acid numbers 1 to 112 of SEQ ID NO: 8, and the CDR1, CDR2, and CDR3 of the light chain respectively consist of the amino acid sequence of amino acid numbers 24 to 38, 54 to 60, and 93 to 101 of SEQ ID NO: 8.

The base sequence of the heavy chain of the prepared humanized antibody CL6_40m16_DDW is shown by SEQ ID NO: 9, the amino acid sequence encoded by the base sequence is shown by SEQ ID NO: 10, the base sequence of the light chain of the antibody is shown by SEQ ID NO: 11, and the amino acid sequence encoded by the base sequence is shown by SEQ ID NO: 12. The variable region of the heavy chain shown by SEQ ID NO: 10 consists of the amino acid sequence of amino acid numbers 1 to 119 of SEQ ID NO: 10, and the CDR1, CDR2, and CDR3 of the heavy chain respectively consist of the amino acid sequence of amino acid numbers 31 to 35, 50 to 65, and 98 to 108 of SEQ ID NO: 10. The variable region of the light chain shown by SEQ ID NO: 12 consists of the amino acid sequence of amino acid numbers 1 to 112 of SEQ ID NO: 12, and the CDR1, CDR2, and CDR3 of the light chain respectively consist of the amino acid sequence of amino acid numbers 24 to 38, 54 to 60, and 93 to 101 of SEQ ID NO: 12.

CDR1, CDR2, and CDR3 of each of heavy chains shown by SEQ ID NOS: 6 and 10 are the same as CDR1, CDR2, and CDR3 of the heavy chain shown by SEQ ID NO: 2, and CDR1, CDR2, and CDR3 of each of light chains shown by SEQ ID NOS: 8 and 12 are the same as CDR1, CDR2, and CDR3 of the light chain shown by SEQ ID NO: 4.

In order to prepare each humanized antibody, the above-described GS vector into which the genes of the heavy chain and the light chain of each antibody were respectively inserted was cleaved with a restriction enzyme by NotI and PvuI, and ligation was performed using a Ligation-Convenience Kit (NIPPONGENE Co., Ltd.), thereby constructing a Double-Gene vector into which both genes of the heavy chain and the light chain were inserted. Next, the Double-Gene vector was transfected using an ExpiFectamine 293 (Life Technologies, Inc.), and cultured for 5 days with respect to Expi 293 cells (Life Technologies, Inc.) cultured in an Expi 293 Expression medium (Life Technologies, Inc.) at approximately 3000000 cells/mL. Next, purified antibodies of respective humanized antibodies were obtained using Protein G (GE Healthcare Japan Corporation) from the obtained culture supernatants. In regard to constitutive expression, antibodies were expressed by transfecting the above-described Double-Gene vector to CHO-K1SV cells (Lonza Biologics, Inc.). Then, purified antibodies of respective humanized antibodies were obtained using MabSelect SuRe (GE Healthcare Japan Corporation) from the culture supernatants. As a result of analyzing amino acid modification of the respective purified humanized antibodies, in most of the purified antibodies, deletion of lysine at the C terminal of the heavy chain occurred in CL6_40m2_DDW, pyroglutamylation at the N terminal of the heavy chain and deletion of lysine at the C terminal of the heavy chain occurred in CL6_40m14_DDW, and deletion of lysine at the C terminal of the heavy chain occurred in CL6_40m16_DDW.

Example 4

ELISA Assay with Respect to Antigen

In order to measure the antigen binding activity of the humanized antibody, antigen ELISA was used. The human Igβ-Flag protein acquired in Example 1 was prepared with a tris-buffered saline (TBS; Wako Pure Chemical Industries, Ltd.) so as to have a concentration of 5000 ng/mL, added to a NUNC MaxiSorp white 384 plate (Maxisorp 384 plate: Nunc Corporation) by an amount of 15 μL per well, and then solidified at room temperature for 1 hour. The resultant was washed with TBS-T (0.05% Tween-20 containing TBS: Wako Pure Chemical Industries, Ltd.) twice, 120 μL of a blocking agent (Blocking One: Nacalai tesque, Inc.) was added thereto, the resultant was left at room temperature for 1 hour, and the solution was removed. A dilution series (8 steps with a final concentration of 0.46 ng/mL to 1 μg/mL) of respective humanized antibodies obtained in Example 3 was prepared using a dilute solution obtained by adding the same amount of the blocking agent and TBS and then added thereto by an amount of 15 μL. The resultant was left at room temperature for 1 hour, washed with a TBS-T washing liquid three times, and 20 μL of an horseradish peroxidase (HRP)-labeled rabbit anti-human Ig antibody (Dako Ltd.) which had been diluted 3000-fold with a diluted solution was added thereto. Thereafter, the resultant was left at room temperature for 1 hour and then washed with a TBS-T washing liquid three times. Next, 30 μL of BM-Chemiluminescence ELISA Substrate (POD) (Roche Diagnostics Inc.) which is a chemiluminescence detection reagent was added thereto, and the amount of chemiluminescence thereof was measured by an EnVision counter (PerkinElmer, Co., Ltd.). Using the same method, antigen ELISA assay was performed using the monkey Igβ-Flag protein acquired in Example 1. When the binding activities in respective concentrations of the test antibodies were calculated, the measuring amount of a well to which a test antibody was not added was set to 0% and the convergence value of the maximum activity of the test antibody was set to 100%. The calculated binding activities were analyzed and the EC50 values of the test antibodies were calculated by fitting a curve.

As a result, the EC50 values with respect to human and monkey Igβ-Flag proteins of CL6_40m12_DDW were respectively 128 ng/mL and 183 ng/mL. The EC50 values with respect to human and monkey Igβ-Flag proteins of CL6_40m14_DDW were respectively 100 ng/mL and 106 ng/mL. The EC50 values with respect to human and monkey Igβ-Flag proteins of CL6_40m16_DDW were respectively 132 ng/mL and 118 ng/mL. It was confirmed that all of the respective humanized antibodies had high binding activities with respect to both of the human and monkey Igβ-Flag proteins.

Example 5

FACS Analysis with Respect to Human and Monkey PBMC

In order to evaluate the binding activities of humanized antibodies with respect to human and monkey cells, Fluorescence Activated Cell Sorting (FACS) analysis was performed on human and monkey PBMC with an index of CD20 which is a B cell marker using B cells contained in the PBMC as a target. The monkey PBMC was prepared by diluting the blood of a monkey in the same amount of PBS (Life Technologies, Inc.), laminating the diluted blood on the same amount of Ficoll (GE Healthcare Japan Corporation), and performing a centrifugal treatment at room temperature and at 1500 rpm for 30 minutes. Next, human PBMC (AllCells, Inc.) or monkey PBMC was seeded by an amount of 200000 per well in a 96-well plate (Greiner Bio-One) in a state of being suspended in 30 μL of Stain Buffer (Becton, Dickinson Company). A dilution series (4 steps with a final concentration of 0.03 ng/mL to 30 μg/mL) of each of the humanized antibodies acquired in Example 3 was prepared using Stain Buffer and 30 μL of the dilution series was added thereto. The resultant was left on ice for 30 minutes, washed with Stain Buffer three times, and 40 μL of a solution having a phycoerythrin-labeled goat anti-human IgG Fcγ fragment (JACKSON, Inc.) which was diluted 200-fold with Stain Buffer and an allophycocyanin-labeled mouse anti-CD20 antibody (Becton, Dickinson Company) diluted 8-fold with Stain Buffer was added thereto. The resultant was left on ice for 30 minutes and washed with Stain Buffer twice, the fluorescence intensity was measured using FACSArray (Becton, Dickinson Company), and then the mean fluorescence intensity: MFI) was calculated. FlowJo (TOMY DIGITAL BIOLOGY Co., Ltd.) was used for analysis.

As a result, it was confirmed that all of the respective humanized antibodies had high binding activities with respect to both of the human and monkey B cells.

Example 6

Evaluation of Anti-IgM Antibody-induced Cell Proliferation Activity

In order to evaluate the inhibitory effect of a humanized antibodies with respect to activation of human B cells due to BCR stimulation, anti-IgM antibody-induced cell proliferation activity in human B cells was evaluated. The anti-IgM antibody activates B cells by allowing BCR to aggregate. An antibody binding to both of BCR and FcγRIIb mobilizes FcγRIIb to BCR and thus proliferation of B cells can be inhibited. In this Example, anti-CD19 S267E/L328F (Patent Document 2) was used as a comparative antibody. As a control antibody, a human IgG1 antibody (anti-KLH Ab) against KLH (keyhole limpet hemocyanin) which is an antigen not existing in a living body was used (WO 2013/094723). Next, human B cells (AllCells, Inc.) were seeded by an amount of 30000 per well in a 96-well plate (Iwaki, Co., Ltd.) using a 60 μL of RPMI culture medium (SIGMA-ALDRICH Corporation). Subsequently, dilution series (3 steps with a final concentration of 0.3 ng/mL to 30 μg/mL) of the respective full human antibodies acquired in Example 3, anti-CD19 S267E/L328F, or anti-KLH Ab were prepared and added thereto by an amount of 20 μL using the RPMI culture medium. 20 μL of the anti-IgM antibody (JACKSON, Inc.) prepared such that the final concentration thereof in the RPMI culture medium was adjusted to 5 μg/mL was added and incubated in a $CO_2$ incubator for 4 days. Next, cell proliferation analysis was performed using CellTiter-Glo (Promega K.K.). In addition, in Example here, a test antibody non-added/anti-IgM antibody non-added group and a test antibody non-added/anti-IgM antibody added group were respectively prepared as a negative control and a positive control and then a test was performed. Respective test antibodies were tested in duplicate.

FIG. 1 shows the results of the proliferation rate of human B cells. The proliferation rates of a test antibody administration group was calculated by setting a test antibody non-added/anti-IgM antibody non-added group as a negative control (proliferation rate: 0%) and a test antibody non-added/anti-IgM antibody added group as a positive control (proliferation rate: 100%). This means that the inhibitory activity with respect to BCR of a test antibody is stronger when the value of the proliferation rate thereof is smaller.

As shown in FIG. 1, while the proliferation rate in 30 μg/mL of anti-CD19 S267E/L328F was 52.3%, the proliferation rates in 30 μg/mL of CL6_40m12_DDW, CL6_40m14_DDW, and CL6_40m16_DDW were respectively 2.8%, 20.2%, and 23.2%. Therefore, it is evident that all of the above-described full human antibodies have strong inhibitory activities with respect to anti-IgM antibody-induced cell proliferation in human B cells compared to anti-CD19 S267E/L328F.

Example 7

Evaluation of Drug Efficacy in Human PBMC Transfer NOG Mouse Model

For the purpose of verifying the effectiveness of a humanized antibody with respect to in vivo antibody production, an action of various antibodies in administration for treatment with respect to an increase in human antibody titers induced by transferring human PBMC into an NOG mouse was evaluated. In the present model, it is considered that the human B cells violently activated by foreign object (mouse) recognition differentiate into plasma (blast) cells in the body of the mouse, and the present model is appropriate for evaluating a pharmacological action of a test drug with respect to the activity of human B series cells.

Human PBMC (AllCells, Inc.) was suspended at 10000000 cells/mL in PBS (Wako Pure Chemical Industries, Ltd.) and administered to the tail vein of a 11-week-old male NOG mouse (In-vivo Science, Inc.) by an amount of 0.25 mL (2500000 cells). On the $34^{th}$ day ($34^{th}$ day after PBMC transfer), the weight was measured and blood was sampled. The plasma human IgM and IgE antibody titer was measured using ELISA (Bethyl Laboratories, Inc.). Grouping was performed based on the plasma human IgM, the IgE antibody titer, and the weight data.

In this Example, as a comparative antibody, anti-CD19 S267E/L328F was used. As a control antibody, anti-KLH Ab was used. 10 mg/10 mL/kg of a test antibody was administered to a mouse by subcutaneous administration on the $35^{th}$ and the $42^{nd}$ days. Blood sampling was performed on the $42^{nd}$ and the $49^{th}$ days and the plasma human IgM and IgE antibody titer was measured using ELISA (Bethyl Laboratories, Inc.). The test was performed in a unit of a group of 4 or 5 animals. The test results are shown by "average value±standard error." A significant difference test of an anti-KLH Ab group and various test antibody groups was performed using a Student's t-test, and a case where the p value was less than 0.05 was regarded as statistically significant. The above-described test was performed using a GraphPad Prism (version 5.04).

Figure 2:
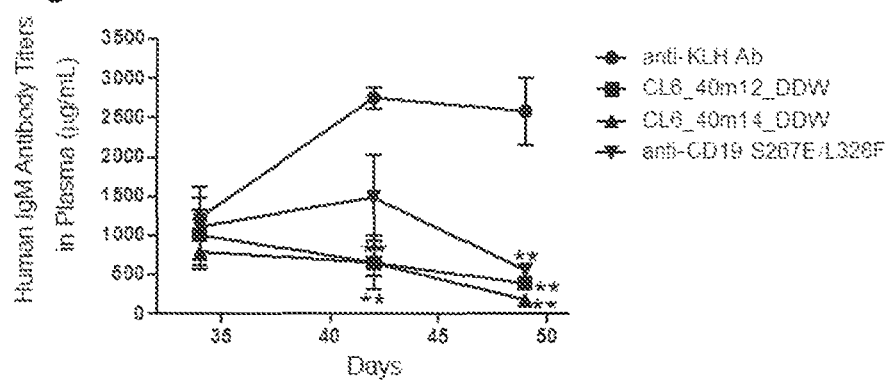
FIG. 2 shows an inhibitory action of a humanized anti-Igβ antibody against an increase in human IgM antibody titers in plasma induced by transfer of human PBMC into an NOG mouse. The vertical axis indicates the human IgM antibody titer in plasma (μg/mL) and the horizontal axis indicates the time (day) from transferring the human PBMC into the NOG mouse.

FIG. 2 shows an action of a test antibody with respect to the plasma human IgM antibody titer. The plasma human IgM antibody titer was significantly decreased by CL6_40m12_DDW and CL6_40m14_DDW compared to anti-KLH Ab. An action of decreasing CL6_40m12_DDW and CL6_40m14_DDW with respect to the plasma human IgM antibody titer was expressed exceedingly early and recognized from the first week after the administration was started ($42^{nd}$ day). Meanwhile, in anti-CD19 S267E/L328F, an action of a decrease with respect to the plasma human IgM antibody titer was significant only after 2 weeks after administration was started ($49^{th}$ day).

Figure 3:
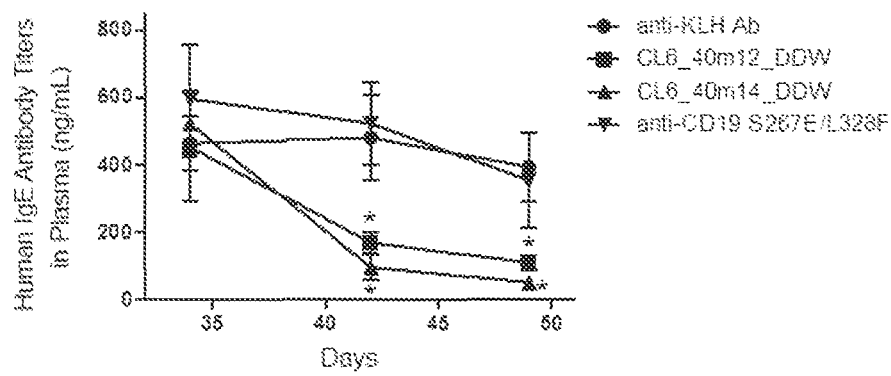
FIG. 3 shows an inhibitory action of a humanized anti-Igβ antibody against an increase in human IgE antibody titers in plasma induced by transfer of human PBMC into an NOG mouse. The vertical axis indicates the human IgE antibody titer in plasma (ng/mL) and the horizontal axis indicates the time (day) from transferring the human PBMC into the NOG mouse.
Figure 4:
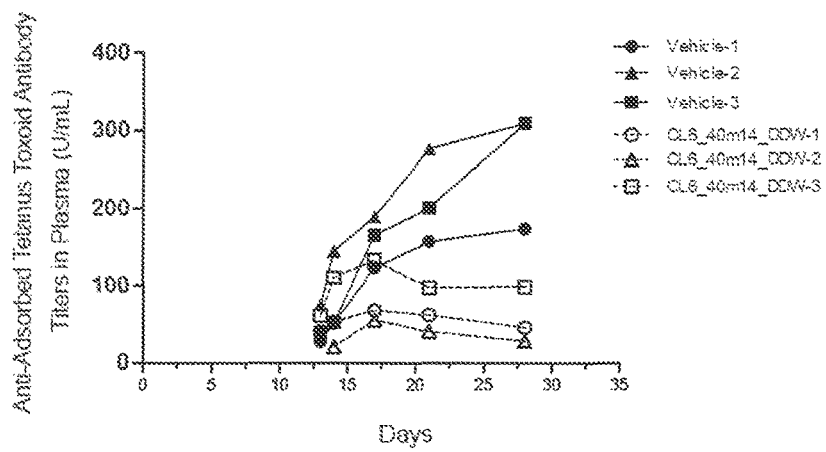
FIG. 4 shows an inhibitory action of a humanized anti-Igβ antibody against an increase in anti-adsorbed tetanus toxoid in plasma caused by immunizing adsorbed tetanus toxoid to a monkey. The vertical axis indicates the anti-adsorbed tetanus toxoid antibody titer in plasma (U/mL) and the horizontal axis indicates the time (day) from immunizing adsorbed tetanus toxoid to a monkey.

Next, FIG. 3 shows an action of a test antibody with respect to the plasma human IgE antibody titer. In CL6_40m12_DDW and CL6_40m14_DDW, the plasma human IgE antibody titer was rapidly and significantly decreased compared to anti-KLH Ab. Meanwhile, in anti-CD19 S267E/L328F, the plasma human IgE antibody titer was not decreased.

As shown in FIGS. 2 and 3, it is evident that both of the above-described CL6_40m12_DDW and CL6_40m14_DDW have strong inhibitory activities with respect to an increase in the human antibody titer compared to anti-CD19 S267E/L328F.

Example 8

Evaluation of Drug Efficacy in Monkey TTx Antigen Sensitization Model

TTx antigen-specific IgG was produced by sensitizing an adsorbed tetanus toxoid (TTx) antigen to a monkey once. In the present model, the total antibody titers in plasma can be evaluated in addition to TTx antigen-specific IgG in plasma. Accordingly, in the present model, safety can be evaluated in addition to effectiveness thereof when autoimmune diseases are treated.

Using a male cynomolgus monkey (producing area: China, 3 years old or older), 2 mg/kg to 5 mg/kg (0.05 ml/kg: USP Corporation) of zolazepam hydrochloride and 2.5 mg/kg to 5 mg/kg of tiletamine hydrochloride were mixed under anesthesia and TTx was sensitized (the sensitization day was set to Day 0). The sensitization of TTx was performed by injecting 0.6 mL/monkey of tetanus toxoid (TTx, 10 Lf/mL, Denka Seika Co., Ltd.) to thigh muscle and 0.6 mL/monkey (respectively 50 μL to 12 places) to the intradermal back portion. As treated groups, a Vehicle group (solvent (20 mM of sodium citrate buffer/120 mM, NaCl (pH: 6.0); KOHJIN BIO Co., Ltd.) 1 mL/kg, n=3) and an antibody administration group (10 mg/1 mL/kg, humanized antibody CL6_40m14_DDW (diluted with solvent), n=3) were used. The timing of administration was set to the $14^{th}$ day after TTx sensitization and the administration to the vein was performed with a dosage of 1 mL/kg when awakening.

After CL6_40m14_DDW was administered to the above-described cynomolgus monkey, blood was sampled with time, for example, after 4 hours, 72 hours, 168 hours, and 336 hours, and was subjected to a centrifugal treatment, and then plasma was recovered. The concentration of drugs in the plasma was measured using Gyrolab™xP workstation (Gyros AB). As the method and the disc, 200-3W-001-A and Bioaffy 200 compact discs (Gyros AB) were used. In addition, as a solidified antigen and a detection antibody, biotin-labeled Recombinant Human CD79B (Novoprotein, Inc.) and alexa-labeled Goat Anti-Human IgG (Southern Biotechnology Associates, Inc.) were used. As listed in Table 1, the concentration of drugs in plasma of CL6_40m14_DDW was maintained during the evaluation period of the model.

Table 1: Transition of concentration of drugs in plasma with respect to humanized anti-Igβ antibody in monkey

TABLE 1

| | Concentration of drugs in plasma of individual 1 (μg/mL) | Concentration of drugs in plasma of individual 2 (μg/mL) | Concentration of drugs in plasma of individual 3 (μg/mL) |
|---|---|---|---|
| After 4 hours | 252.111 | 263.242 | 258.271 |
| After 72 hours | 143.586 | 144.095 | 114.605 |
| After 168 hours | 120.070 | 112.865 | 95.848 |
| After 336 hours | 76.854 | 62.281 | 53.305 |

Blood was sampled from the above-described cynomolgus monkey with time on the $13^{th}$ day (13 days after the cynomolgus was immunized by adsorbed tetanus toxoid), the $14^{th}$ day, the $17^{th}$ day, the $21^{st}$ day, and the $28^{st}$ day, a centrifugal treatment was carried out, and plasma was recovered. In order to measure anti-adsorbed tetanus toxoid (anti-TTx IgG) in the recovered plasma, the antigen ELISA was used. The adsorbed tetanus toxoid (Denka Seika Co., Ltd.) was diluted 20-fold with a phosphate-buffered saline (PBS; Wako Pure Chemical Industries, Ltd.), was added to a NUNC MaxiSorp 96 plate (Maxisorp 96 plate: Nunc Corporation) by an amount of 100 μL per well, and then solidified at 4° C. for one night. The resultant was washed with PBS-T (0.05% Tween-20 containing PBS: Thermo Scientific, Inc.) four times, 200 μL of a blocking agent (Blocker Casein In PBS; Life Technologies, Inc.) was added thereto, the resultant was left at room temperature for 2 hour, and the solution was removed. Next, 100 μL of the recovered plasma and 100 μL of a sample for a calibration curve were respectively added thereto. As the sample for a calibration curve, a sample mixed with plasma collected 21 days and 23 days later from immunization of the cynomolgus monkey by adsorbed tetanus toxoid was used, the amount thereof was adjusted to 100 U/mL, and a dilution series (0.488 mU/mL to 500 mU/mL) prepared using a blocking agent as a diluted solution was used. The resultant was left at room temperature for 2 hour, washed with a PBS-T washing liquid four times, and 100 μL of a horseradish peroxidase (HRP)-labeled goat anti-monkey IgG antibody (Nordic, Inc.) which had been diluted 3000-fold with a blocking agent was added thereto. Thereafter, the resultant was left at room temperature for 1 hour and then washed with the PBS-T washing liquid four times. Next, measurement was performed using TMB Microwell Peroxidase Substrate System (KPL, Inc.). The absorbance thereof was measured by SpectraMax (Molecular Devices, Inc.).

FIG. 4 shows an action of the test antibody with respect to the adsorbed tetanus toxoid antibody titer in plasma. The adsorbed tetanus toxoid antibody titer in plasma (anti-TTX IgG) was decreased in CL6-40m14_DDW compared to the Vehicle group.

The total antibody titers (IgM, IgA, and IgG) in plasma recovered from the cynomolgus monkey on the $14^{th}$ day, the $17^{th}$ day, the $21^{st}$ day, and the 28 day were measured using the following method. A rabbit anti-monkey IgM polyclonal antibody (COVANCE, Inc.) and a rabbit anti-human IgA polyclonal antibody (Bethyl Laboratories, Inc.) were diluted 100-fold, 500-fold, and 1000-fold with a phosphate-buffered saline (PBS: Wako Pure Chemical Industries, Ltd.), added to a NUNC MaxiSorp 96 plate (Maxisorp 96 plate: Nunc Corporation) by an amount of 100 μL, and then solidified at 4° C. for one night. The resultant was washed with PBS-T (0.05% Tween-20 containing PBS: Thermo Scientific, Inc.) four times, 200 μL of a blocking agent (Blocker Casein In PBS; Life Technologies, Inc.) was added thereto, and the resultant was left at room temperature for 1 hour and washed with the PBS-T washing liquid for times. A dilution series of a sample for a calibration curve and collected plasma of a monkey was prepared using a blocking agent as a diluted solution and 100 μL of the dilution series was added thereto. As the sample for a calibration curve, plasma prepared from a normal cynomolgus monkey was diluted and then used. The resultant was left at room temperature for 2 hour, washed with a PBS-T washing liquid four times, and an horseradish peroxidase (HRP)-labeled anti-monkey IgM antibody (KPL, Inc.), an horseradish peroxidase (HRP)-labeled anti-human IgA antibody (Bethyl Laboratories, Inc.), and a horseradish peroxidase (HRP)-labeled anti-monkey IgG antibody (KPL, Inc.) were respectively diluted 1000-fold, 5000-fold, and 3000-fold with a blocking agent and added thereto by an amount of 100 μL respectively. Thereafter, the resultant was left at room temperature for 2 hours and then washed with a PBS-T washing liquid four times. Next, measurement was performed using TMB Microwell Peroxidase Substrate System (KPL, Inc.). The absorbance thereof was measured by SpectraMax (Molecular Devices, Inc.).

Figure 5:
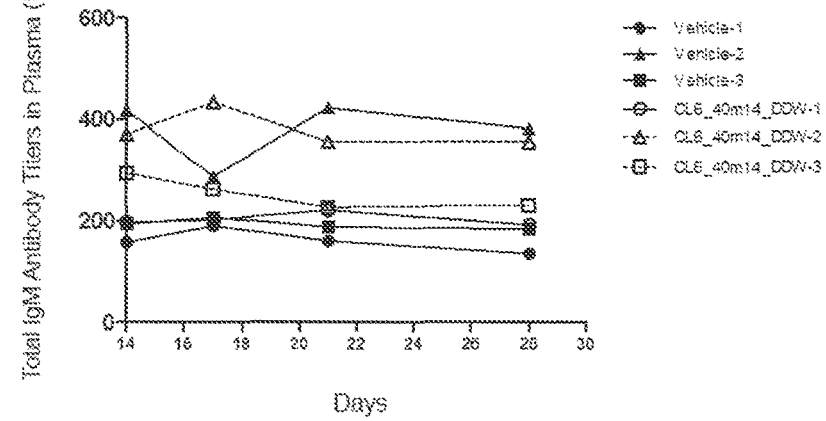
FIG. 5 shows an action of the humanized anti-Igβ antibody against total IgM antibody titer in plasma of the monkey immunized by adsorbed tetanus toxoid. The vertical axis indicates the total IgM antibody titer in plasma (U/mL) and the horizontal axis indicates the time (day) from immunizing adsorbed tetanus toxoid to a monkey.
Figure 6:
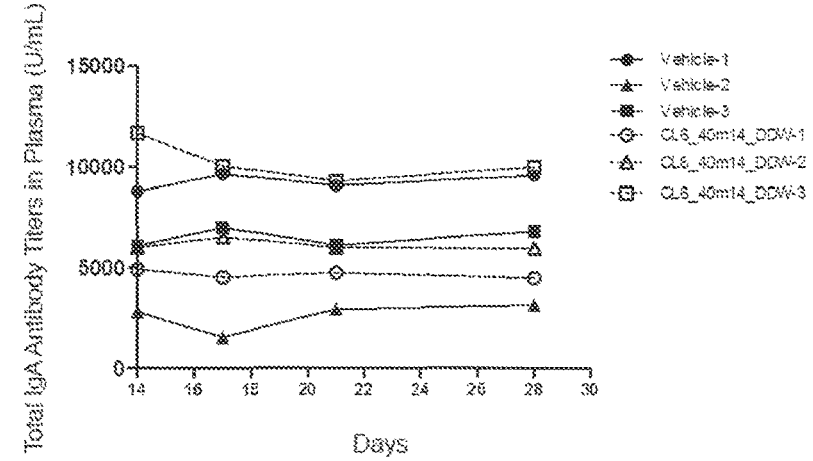
FIG. 6 shows an action of the humanized anti-Igβ antibody against total IgA antibody titer in plasma of the monkey immunized by adsorbed tetanus toxoid. The vertical axis indicates the total IgA antibody titer in plasma (U/mL) and the horizontal axis indicates the time (day) from immunizing adsorbed tetanus toxoid to a monkey.

FIGS. 5, 6, and 7 show actions of the test antibodies with respect to the total antibody titers (IgM, IgA, and IgG) in plasma. CL6_40m14_DDW did not affect the total antibody titers (IgM, IgA, and IgG) in plasma compared to the Vehicle group.

From the results described above, it is evident that CL6_40m14_DDW suppresses an antigen-specific antibody without affecting the total antibody titers in plasma. Further, it is also evident that CL6_40m14_DDW has an excellent profile in terms of safety in addition to effectiveness at the time of treatment of autoimmune diseases.

INDUSTRIAL APPLICABILITY

The anti-human Igβ antibody of the present invention is useful for preventing and treating autoimmune diseases. Further, the polynucleotide, the expression vectors, the transformed host cell, and the methods for producing the antibody of the present invention are useful for producing the anti-human Igβ antibody.

Sequence List Free Text

In the number heading <223> of the sequence list, description of "Artificial Sequence" is made. Specifically, the base sequences shown by SEQ ID NOS: 1 and 3 of the sequence list are the base sequences of the heavy chain and the light chain of the CL6_40m12_DDW, respectively, and the amino acid sequences shown by SEQ ID NOS: 2 and 4 are the amino acid sequences of the heavy chain and the light chain encoded by the SEQ ID NOS: 1 and 3, respectively. The base sequences shown by SEQ ID NOS: 5 and 7 of the sequence list are the base sequences of the heavy chain and the light chain of the CL6_40m14_DDW, respectively, and the amino acid sequences shown by SEQ ID NOS: 6 and 8 are the amino acid sequences of the heavy chain and the light chain encoded by the SEQ ID NOS: 5 and 7, respectively. The base sequences shown by SEQ ID NOS: 9 and 11 of the sequence list are the base sequences of the heavy chain and the light chain of the CL6_40m16_DDW, respectively, and the amino acid sequences shown by SEQ ID NOS: 10 and 12 of the sequence list are the amino acid sequences of the heavy chain and the light chain encoded by the SEQ ID NOS: 9 and 11, respectively. The base sequence shown by SEQ ID NO: 13 of the sequence list is the base sequence of the human Igβ-Flag gene and the base sequence shown by SEQ ID NO: 14 of the sequence list is the base sequence of the monkey Igβ-Flag gene. The base sequence shown by SEQ ID NO: 15 of the sequence list is the base sequence of the heavy chain of the CL6_40m12_DDW.

The invention claimed is:

1. An anti-human Igβ antibody comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 108 of SEQ ID NO: 2, a light chain variable region comprising CDR1 consisting of the amino acid sequence of amino acid numbers 24 to 38 of SEQ ID NO: 4, CDR2 consisting of the amino acid sequence of amino acid numbers 54 to 60 of SEQ ID NO: 4, and CDR3 consisting of the amino acid sequence of amino acid numbers 93 to 101 of SEQ ID NO: 4, and a heavy chain constant region which is a human Igγ1 constant region having amino acid mutations of S239D, H268D, and L328W.

2. The anti-human Igβ antibody according to claim 1, selected from the group consisting of the following (a) to (d):
(a) an anti-human Igβ antibody comprising a heavy chain variable region consisting of the amino acid sequence of amino acid numbers 1 to 119 of SEQ ID NO: 6, a light chain variable region consisting of the amino acid sequence of amino acid numbers 1 to 112 of SEQ ID NO: 8, and a heavy chain constant region which is a human Igγ1 constant region having amino acid mutations of S239D, H268D, and L328W;
(b) an anti-human Igβ antibody comprising a heavy chain variable region consisting of the amino acid sequence of amino acid numbers 1 to 119 of SEQ ID NO: 2, a light chain variable region consisting of the amino acid sequence of amino acid numbers 1 to 112 of SEQ ID NO: 4, and a heavy chain constant region which is a human Igγ1 constant region having amino acid mutations of S239D, H268D, and L328W;
(c) an anti-human Igβ antibody comprising a heavy chain variable region consisting of the amino acid sequence of amino acid numbers 1 to 119 of SEQ ID NO: 10, and a light chain variable region consisting of the amino acid sequence of amino acid numbers 1 to 112 of SEQ ID NO: 12, and a heavy chain constant region which is a human Igγ1 constant region having amino acid mutations of S239D, H268D, and L328W; and
(d) an anti-human Igβ antibody which is derived from posttranslational modification of the anti-human Igβ antibody of any one of (a) to (c) above, wherein the posttranslational modification is pyroglutamylation at the N terminal of the heavy chain variable region and/or deletion of lysine at the C terminal of the heavy chain.

3. The anti-human Igβ antibody according to claim 2, selected from the group consisting of the following (a) to (d):
(a) an anti-human Igβ antibody comprising a heavy chain consisting of the amino acid sequence shown by SEQ ID NO: 6 and a light chain consisting of the amino acid sequence shown by SEQ ID NO: 8;

(b) an anti-human Igβ antibody comprising a heavy chain consisting of the amino acid sequence shown by SEQ ID NO: 2 and a light chain consisting of the amino acid sequence shown by SEQ ID NO: 4;

(c) an anti-human Igβ antibody comprising a heavy chain consisting of the amino acid sequence shown by SEQ ID NO: 10 and a light chain consisting of the amino acid sequence shown by SEQ ID NO: 12; and (d) an anti-human Igβ antibody which is derived from posttranslational modification of the anti-human Igβ antibody of any one of (a) to (c) above, wherein the posttranslational modification is pyroglutamylation at the N terminal of the heavy chain variable region and/or deletion of lysine at the C terminal of the heavy chain.

4. The anti-human Igβ antibody according to claim 2, selected from the group consisting of the following (a) to (f):

(a) an anti-human Igβ antibody comprising a heavy chain consisting of the amino acid sequence shown by SEQ ID NO: 6 and a light chain consisting of the amino acid sequence shown by SEQ ID NO: 8;

(b) an anti-human Igβ antibody comprising a heavy chain consisting of the amino acid sequence of amino acid numbers 1 to 448 of SEQ ID NO: 6 in which glutamine of amino acid number 1 is modified to pyroglutamic acid and a light chain consisting of the amino acid sequence shown by SEQ ID NO: 8;

(c) an anti-human Igβ antibody comprising a heavy chain consisting of the amino acid sequence shown by SEQ ID NO: 2 and a light chain consisting of the amino acid sequence shown by SEQ ID NO: 4;

(d) an anti-human Igβ antibody comprising a heavy chain consisting of the amino acid sequence of amino acid numbers 1 to 448 of SEQ ID NO: 2 and a light chain consisting of the amino acid sequence shown by SEQ ID NO: 4;

(e) an anti-human Igβ antibody comprising a heavy chain consisting of the amino acid sequence shown by SEQ ID NO: 10 and a light chain consisting of the amino acid sequence shown by SEQ ID NO: 12; and (f) an anti-human Igβ antibody comprising a heavy chain consisting of the amino acid sequence of amino acid numbers 1 to 448 of SEQ ID NO: 10 and a light chain consisting of the amino acid sequence shown by SEQ ID NO: 12.

5. The anti-human Igβ antibody according to claim 4, wherein the anti-human Igβ antibody comprises a heavy chain consisting of the amino acid sequence shown by SEQ ID NO: 6 and a light chain consisting of the amino acid sequence shown by SEQ ID NO: 8.

6. The anti-human Igβ antibody according to claim 4, wherein the anti-human Igβ antibody comprises a heavy chain consisting of the amino acid sequence of amino acid numbers of 1 to 448 of SEQ ID NO: 6 in which glutamine of amino acid number 1 is modified to pyroglutamic acid and a light chain consisting of the amino acid sequence shown by SEQ ID NO: 8.

7. The anti-human Igβ antibody according to claim 2, wherein the antibody is fused to another peptide.

8. The anti-human Igβ antibody according to claim 2, wherein the antibody is modified with polyethylene glycol, sugar chains, phospholipids, liposomes, or low-molecular compounds.

9. A pharmaceutical composition comprising: an anti-human Igβ antibody according to claim 1, and a pharmaceutically acceptable excipient.

10. A pharmaceutical composition comprising an anti-human Igβ antibody selected from the group consisting of the following (a) to (c), and a pharmaceutically acceptable excipient:

(a) an anti-human Igβ antibody comprising a heavy chain consisting of the amino acid sequence shown by SEQ ID NO: 6 and a light chain consisting of the amino acid sequence shown by SEQ ID NO: 8, and/or an anti-human Igβ antibody comprising a heavy chain consisting of the amino acid sequence of amino acid numbers of 1 to 448 of SEQ ID NO: 6 in which glutamine of amino acid number 1 is modified to pyroglutamic acid and a light chain consisting of the amino acid sequence shown by SEQ ID NO: 8;

(b) an anti-human Igβ antibody comprising a heavy chain consisting of the amino acid sequence shown by SEQ ID NO: 2 and a light chain consisting of the amino acid sequence shown by SEQ ID NO: 4, and/or an anti-human Igβ antibody comprising a heavy chain consisting of the amino acid sequence of amino acid numbers 1 to 448 of SEQ ID NO: 2 and a light chain consisting of the amino acid sequence shown by SEQ ID NO: 4; and (c) an anti-human Igβ antibody comprising a heavy chain consisting of the amino acid sequence shown by SEQ ID NO: 10 and a light chain consisting of the amino acid sequence shown by SEQ ID NO: 12, and/or an anti-human Igβ antibody comprising a heavy chain consisting of the amino acid sequence of amino acid numbers 1 to 448 of SEQ ID NO: 10 and a light chain consisting of the amino acid sequence shown by SEQ ID NO: 12.

* * * * *

UNITED STATES PATENT AND TRADEMARK OFFICE
CERTIFICATE OF CORRECTION

PATENT NO. : 10,316,086 B2
APPLICATION NO. : 15/501626
DATED : June 11, 2019
INVENTOR(S) : Yamajuku et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 210 days.

Signed and Sealed this
Nineteenth Day of May, 2020

Andrei Iancu
*Director of the United States Patent and Trademark Office*

SEQUENCE LISTING

```
<160> NUMBER OF SEQ ID NOS: 15

<210> SEQ ID NO 1
<211> LENGTH: 1350
<212> TYPE: DNA
<213> ORGANISM: Artificial Sequence
<220> FEATURE:
<223> OTHER INFORMATION: H-chain of anti-human Ig-beta antibody
<220> FEATURE:
<221> NAME/KEY: CDS
<222> LOCATION: (1)..(1350)

<400> SEQUENCE: 1 gag gtg cag atg gtc gag agc ggg ggg ggc ctg gtg cag cct ggg ggt      48
Glu Val Gln Met Val Glu Ser Gly Gly Gly Leu Val Gln Pro Gly Gly
1               5                   10                  15 tcc ctg aga ctg tct tgt gcc gtg tcc ggg ttt tca ctg tcc agc tat      96
Ser Leu Arg Leu Ser Cys Ala Val Ser Gly Phe Ser Leu Ser Ser Tyr
            20                  25                  30 agt gtg cac tgg gtc cga cag gca cca ggg aag ggt ctg gag tgg gtg     144
Ser Val His Trp Val Arg Gln Ala Pro Gly Lys Gly Leu Glu Trp Val
        35                  40                  45 gca gga atc tgg tca gga gga tcc att cat tat acc cct gcc ctg tct     192
Ala Gly Ile Trp Ser Gly Gly Ser Ile His Tyr Thr Pro Ala Leu Ser
    50                  55                  60 agt aga ttc aca gtg agc cgc gac gat tct aaa aac aca gtc tac ctg     240
Ser Arg Phe Thr Val Ser Arg Asp Asp Ser Lys Asn Thr Val Tyr Leu
65                  70                  75                  80 cag atg aat agc ctg agg gcc gag gac acc gct gtc tac tat tgc gct     288
Gln Met Asn Ser Leu Arg Ala Glu Asp Thr Ala Val Tyr Tyr Cys Ala
                85                  90                  95 aga tac gac cgg tat gaa act tac gca atg gat tac tgg ggc cag gga     336
Arg Tyr Asp Arg Tyr Glu Thr Tyr Ala Met Asp Tyr Trp Gly Gln Gly
            100                 105                 110
```

| | | |
|---|---|---|
| acc ctg gtc acc gtc tcc tca gcc tcc acc aag ggc cca tcg gtc ttc<br>Thr Leu Val Thr Val Ser Ser Ala Ser Thr Lys Gly Pro Ser Val Phe<br>115                     120                    125 | | 384 |
| ccc ctg gca ccc tcc tcc aag agc acc tct ggg ggc aca gcg gcc ctg<br>Pro Leu Ala Pro Ser Ser Lys Ser Thr Ser Gly Gly Thr Ala Ala Leu<br>130                     135                    140 | | 432 |
| ggc tgc ctg gtc aag gac tac ttc ccc gaa ccg gtg acg gtg tcg tgg<br>Gly Cys Leu Val Lys Asp Tyr Phe Pro Glu Pro Val Thr Val Ser Trp<br>145                     150                                160 | | 480 |
| aac tca ggc gcc ctg acc agc ggc gtg cac acc ttc ccg gct gtc cta<br>Asn Ser Gly Ala Leu Thr Ser Gly Val His Thr Phe Pro Ala Val Leu<br>                 165                     170                    175 | | 528 |
| cag tcc tca gga ctc tac tcc ctt agt agc gtg gtg acc gtg ccc tcc<br>Gln Ser Ser Gly Leu Tyr Ser Leu Ser Ser Val Val Thr Val Pro Ser<br>                 180                     185                    190 | | 576 |
| agc agc ttg ggc acc cag acc tac atc tgc aac gtg aat cac aag ccc<br>Ser Ser Leu Gly Thr Gln Thr Tyr Ile Cys Asn Val Asn His Lys Pro<br>                 195                     200                    205 | | 624 |
| agc aac acc aag gtg gac aag aaa gtt gag ccc aaa tct tgt gac aaa<br>Ser Asn Thr Lys Val Asp Lys Lys Val Glu Pro Lys Ser Cys Asp Lys<br>          210                     215                    220 | | 672 |
| act cac aca tgc cca ccg tgc cca gca cct gaa ctc ctg ggg gga ccg<br>Thr His Thr Cys Pro Pro Cys Pro Ala Pro Glu Leu Leu Gly Gly Pro<br>225                     230                     235                    240 | | 720 |
| gac gtc ttc ctc ttc ccc cca aaa ccc aag gac acc ctc atg atc tcc<br>Asp Val Phe Leu Phe Pro Pro Lys Pro Lys Asp Thr Leu Met Ile Ser<br>                         245                     250                    255 | | 768 |
| cgg acc cct gag gtc aca tgc gtg gtg gtg gac gtg agc gac gaa gac<br>Arg Thr Pro Glu Val Thr Cys Val Val Val Asp Val Ser Asp Glu Asp<br>                 260                     265                    270 | | 816 |
| cct gag gtc aag ttc aac tgg tac gtg gac ggc gtg gag gtg cat aat<br>Pro Glu Val Lys Phe Asn Trp Tyr Val Asp Gly Val Glu Val His Asn<br>                 275                     280                    285 | | 864 |
| gcc aag aca aag ccg cgg gag gag cag tac aac agc acg tac cgt gtg<br>Ala Lys Thr Lys Pro Arg Glu Glu Gln Tyr Asn Ser Thr Tyr Arg Val<br>          290                     295                    300 | | 912 |
| gtc agc gtc ctc acc gtc ctg cac cag gac tgg ctg aat ggc aag gag<br>Val Ser Val Leu Thr Val Leu His Gln Asp Trp Leu Asn Gly Lys Glu<br>305                     310                     315                    320 | | 960 |
| tac aag tgc aag gtc tcc aac aaa gcc tgg cca gcc ccc atc gag aaa<br>Tyr Lys Cys Lys Val Ser Asn Lys Ala Trp Pro Ala Pro Ile Glu Lys<br>                         325                     330                    335 | | 1008 |
| acc atc tcc aaa gcc aaa ggg cag ccc cga gaa cca cag gtg tac acc<br>Thr Ile Ser Lys Ala Lys Gly Gln Pro Arg Glu Pro Gln Val Tyr Thr<br>                 340                     345                    350 | | 1056 |
| ctg ccc cca tcc cgg gat gag ctg acc aag aac cag gtc agc ctg acc<br>Leu Pro Pro Ser Arg Asp Glu Leu Thr Lys Asn Gln Val Ser Leu Thr<br>                 355                     360                    365 | | 1104 |
| tgc ctg gtc aaa ggc ttc tat ccc agc gac atc gcc gtg gag tgg gag<br>Cys Leu Val Lys Gly Phe Tyr Pro Ser Asp Ile Ala Val Glu Trp Glu<br>          370                     375                    380 | | 1152 |
| agc aat ggg cag ccg gag aac aac tac aag acc acg cct ccc gtg ctg<br>Ser Asn Gly Gln Pro Glu Asn Asn Tyr Lys Thr Thr Pro Pro Val Leu<br>385                     390                     395                    400 | | 1200 |
| gac tcc gac ggc tcc ttc ttc ctc tac agc aag ctc acc gtg gac aag<br>Asp Ser Asp Gly Ser Phe Phe Leu Tyr Ser Lys Leu Thr Val Asp Lys<br>                         405                     410                    415 | | 1248 |
| agc agg tgg cag cag ggg aac gtc ttc tca tgc tcc gtg atg cat gag<br>Ser Arg Trp Gln Gln Gly Asn Val Phe Ser Cys Ser Val Met His Glu<br>                 420                     425                    430 | | 1296 |

-continued

```
gct ctg cac aac cac tac acg cag aag agc ctc tcc ctg tct ccg ggt      1344
Ala Leu His Asn His Tyr Thr Gln Lys Ser Leu Ser Leu Ser Pro Gly
        435                 440                 445 aaa tga                                                               1350
Lys
```

<210> SEQ ID NO 2
<211> LENGTH: 449
<212> TYPE: PRT
<213> ORGANISM: Artificial Sequence
<220> FEATURE:
<223> OTHER INFORMATION: Synthetic Construct

<400> SEQUENCE: 2

```
Glu Val Gln Met Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ser Val His Trp Val Arg Gln Ala Pro Gly Lys Gly Leu Glu Trp Val
        35                  40                  45

Ala Gly Ile Trp Ser Gly Gly Ser Ile His Tyr Thr Pro Ala Leu Ser
    50                  55                  60

Ser Arg Phe Thr Val Ser Arg Asp Asp Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Tyr Asp Arg Tyr Glu Thr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Trp Pro Ala Pro Ile Glu Lys
```

```
              325                 330                 335
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 3
<211> LENGTH: 657
<212> TYPE: DNA
<213> ORGANISM: Artificial Sequence
<220> FEATURE:
<223> OTHER INFORMATION: L-chain of anti-human Ig-beta antibody
<220> FEATURE:
<221> NAME/KEY: CDS
<222> LOCATION: (1)..(657)

<400> SEQUENCE: 3 gac atc cag ctg acc cag tcc ccc tcc agc ctg tcc gcc tct gtg ggc     48
Asp Ile Gln Leu Thr Gln Ser Pro Ser Ser Leu Ser Ala Ser Val Gly
1               5                   10                  15 gac aga gtg acc atc aca tgc aag gcc tcc cag tcc gtg gac tac gac     96
Asp Arg Val Thr Ile Thr Cys Lys Ala Ser Gln Ser Val Asp Tyr Asp
            20                  25                  30 ggc gac tcc tac atg aac tgg tat cag cag aag ccc ggc aag gcc ccc    144
Gly Asp Ser Tyr Met Asn Trp Tyr Gln Gln Lys Pro Gly Lys Ala Pro
        35                  40                  45 aag ctg ctg atc tac gcc gcc tcc aac ctg gaa tcc ggc gtg ccc tcc    192
Lys Leu Leu Ile Tyr Ala Ala Ser Asn Leu Glu Ser Gly Val Pro Ser
    50                  55                  60 aga ttc tcc ggc tcc ggc tct ggc acc gac ttc acc ctg acc atc tcc    240
Arg Phe Ser Gly Ser Gly Ser Gly Thr Asp Phe Thr Leu Thr Ile Ser
65                  70                  75                  80 agc ctg cag ccc gag gac ttc gcc acc tac tac tgc cag cag tcc aac    288
Ser Leu Gln Pro Glu Asp Phe Ala Thr Tyr Tyr Cys Gln Gln Ser Asn
                85                  90                  95 gag gac ccc ctg acc ttc ggc cag ggc acc aag gtg gaa atc aag cgt    336
Glu Asp Pro Leu Thr Phe Gly Gln Gly Thr Lys Val Glu Ile Lys Arg
            100                 105                 110 acg gtg gct gca cca tct gtc ttc atc ttc ccg cca tct gat gag cag    384
Thr Val Ala Ala Pro Ser Val Phe Ile Phe Pro Pro Ser Asp Glu Gln
        115                 120                 125 ttg aaa tct gga act gcc tct gtt gtg tgc ctg ctg aat aac ttc tat    432
Leu Lys Ser Gly Thr Ala Ser Val Val Cys Leu Leu Asn Asn Phe Tyr
    130                 135                 140 ccc aga gag gcc aaa gta cag tgg aag gtg gat aac gcc ctc caa tcg    480
Pro Arg Glu Ala Lys Val Gln Trp Lys Val Asp Asn Ala Leu Gln Ser
145                 150                 155                 160 ggt aac tcc cag gag agt gtc aca gag cag gac agc aag gac agc acc    528
```

```
Gly Asn Ser Gln Glu Ser Val Thr Glu Gln Asp Ser Lys Asp Ser Thr
                165                 170                 175 tac agc ctc agc agc acc ctg acg ctg agc aaa gca gac tac gag aaa    576
Tyr Ser Leu Ser Ser Thr Leu Thr Leu Ser Lys Ala Asp Tyr Glu Lys
            180                 185                 190 cac aaa gtc tac gcc tgc gaa gtc acc cat cag ggc ctg agc tcg ccc    624
His Lys Val Tyr Ala Cys Glu Val Thr His Gln Gly Leu Ser Ser Pro
        195                 200                 205 gtc aca aag agc ttc aac agg gga gag tgt tag                        657
Val Thr Lys Ser Phe Asn Arg Gly Glu Cys
    210                 215
```

<210> SEQ ID NO 4
<211> LENGTH: 218
<212> TYPE: PRT
<213> ORGANISM: Artificial Sequence
<220> FEATURE:
<223> OTHER INFORMATION: Synthetic Construct

<400> SEQUENCE: 4

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 5
<211> LENGTH: 1350
<212> TYPE: DNA
<213> ORGANISM: Artificial Sequence
<220> FEATURE:
<223> OTHER INFORMATION: H-chain of anti-human Ig-beta antibody
<220> FEATURE:
<221> NAME/KEY: CDS
<222> LOCATION: (1)..(1350)

<400> SEQUENCE: 5

-continued

```
cag gtg cag atg cag gaa tcc ggt ccc ggg ctg gtc cgt cct agc cag      48
Gln Val Gln Met Gln Glu Ser Gly Pro Gly Leu Val Arg Pro Ser Gln
1               5                   10                  15 act ctg tca ctg act tgt act gtc tca ggg ttc tca ctg tcc agc tat      96
Thr Leu Ser Leu Thr Cys Thr Val Ser Gly Phe Ser Leu Ser Ser Tyr
            20                  25                  30 tcc gtg cac tgg gtc aga cag cca cct gga cga gga ctg gag tgg atc     144
Ser Val His Trp Val Arg Gln Pro Pro Gly Arg Gly Leu Glu Trp Ile
        35                  40                  45 ggc gga att tgg agc ggg ggt tct atc cat tac aca cca gct ctg tct     192
Gly Gly Ile Trp Ser Gly Gly Ser Ile His Tyr Thr Pro Ala Leu Ser
    50                  55                  60 agt cga gtg act gtc ctg agg gac acc agt aag aac cag gtg agc ctg     240
Ser Arg Val Thr Val Leu Arg Asp Thr Ser Lys Asn Gln Val Ser Leu
65                  70                  75                  80 aga ctg tca tcc gtc acc gcc gct gat aca gca gtg tac tat tgc gcc     288
Arg Leu Ser Ser Val Thr Ala Ala Asp Thr Ala Val Tyr Tyr Cys Ala
                85                  90                  95 aga tac gac cgg tat gaa acc tac gca atg gat tat tgg ggc cag ggc     336
Arg Tyr Asp Arg Tyr Glu Thr Tyr Ala Met Asp Tyr Trp Gly Gln Gly
            100                 105                 110 tct ctg gtc acc gtc tcc tca gcc tcc acc aag ggc cca tcg gtc ttc     384
Ser Leu Val Thr Val Ser Ser Ala Ser Thr Lys Gly Pro Ser Val Phe
        115                 120                 125 ccc ctg gca ccc tcc tcc aag agc acc tct ggg ggc aca gcg gcc ctg     432
Pro Leu Ala Pro Ser Ser Lys Ser Thr Ser Gly Gly Thr Ala Ala Leu
    130                 135                 140 ggc tgc ctg gtc aag gac tac ttc ccc gaa ccg gtg acg gtg tcg tgg     480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta     528
Asn Ser Gly Ala Leu Thr Ser Gly Val His Thr Phe Pro Ala Val Leu
                165                 170                 175 cag tcc tca gga ctc tac tcc ctt agt agc gtg gtg acc gtg ccc tcc     576
Gln Ser Ser Gly Leu Tyr Ser Leu Ser Ser Val Val Thr Val Pro Ser
            180                 185                 190 agc agc ttg ggc acc cag acc tac atc tgc aac gtg aat cac aag ccc     624
Ser Ser Leu Gly Thr Gln Thr Tyr Ile Cys Asn Val Asn His Lys Pro
        195                 200                 205 agc aac acc aag gtg gac aag aaa gtt gag ccc aaa tct tgt gac aaa     672
Ser Asn Thr Lys Val Asp Lys Lys Val Glu Pro Lys Ser Cys Asp Lys
    210                 215                 220 act cac aca tgc cca ccg tgc cca gca cct gaa ctc ctg ggg gga ccg     720
Thr His Thr Cys Pro Pro Cys Pro Ala Pro Glu Leu Leu Gly Gly Pro
225                 230                 235                 240 gac gtc ttc ctc ttc ccc cca aaa ccc aag gac acc ctc atg atc tcc     768
Asp Val Phe Leu Phe Pro Pro Lys Pro Lys Asp Thr Leu Met Ile Ser
                245                 250                 255 cgg acc cct gag gtc aca tgc gtg gtg gtg gac gtg agc gac gaa gac     816
Arg Thr Pro Glu Val Thr Cys Val Val Val Asp Val Ser Asp Glu Asp
            260                 265                 270 cct gag gtc aag ttc aac tgg tac gtg gac ggc gtg gag gtg cat aat     864
Pro Glu Val Lys Phe Asn Trp Tyr Val Asp Gly Val Glu Val His Asn
        275                 280                 285 gcc aag aca aag ccg cgg gag gag cag tac aac agc acg tac cgt gtg     912
Ala Lys Thr Lys Pro Arg Glu Glu Gln Tyr Asn Ser Thr Tyr Arg Val
    290                 295                 300 gtc agc gtc ctc acc gtc ctg cac cag gac tgg ctg aat ggc aag gag     960
Val Ser Val Leu Thr Val Leu His Gln Asp Trp Leu Asn Gly Lys Glu
```

```
                305                 310                 315                 320
tac aag tgc aag gtc tcc aac aaa gcc tgg cca gcc ccc atc gag aaa         1008
Tyr Lys Cys Lys Val Ser Asn Lys Ala Trp Pro Ala Pro Ile Glu Lys
                    325                 330                 335 acc atc tcc aaa gcc aaa ggg cag ccc cga gaa cca cag gtg tac acc         1056
Thr Ile Ser Lys Ala Lys Gly Gln Pro Arg Glu Pro Gln Val Tyr Thr
            340                 345                 350 ctg ccc cca tcc cgg gat gag ctg acc aag aac cag gtc agc ctg acc         1104
Leu Pro Pro Ser Arg Asp Glu Leu Thr Lys Asn Gln Val Ser Leu Thr
                355                 360                 365 tgc ctg gtc aaa ggc ttc tat ccc agc gac atc gcc gtg gag tgg gag         1152
Cys Leu Val Lys Gly Phe Tyr Pro Ser Asp Ile Ala Val Glu Trp Glu
        370                 375                 380 agc aat ggg cag ccg gag aac aac tac aag acc acg cct ccc gtg ctg         1200
Ser Asn Gly Gln Pro Glu Asn Asn Tyr Lys Thr Thr Pro Pro Val Leu
385                 390                 395                 400 gac tcc gac ggc tcc ttc ttc ctc tac agc aag ctc acc gtg gac aag         1248
Asp Ser Asp Gly Ser Phe Phe Leu Tyr Ser Lys Leu Thr Val Asp Lys
                    405                 410                 415 agc agg tgg cag cag ggg aac gtc ttc tca tgc tcc gtg atg cat gag         1296
Ser Arg Trp Gln Gln Gly Asn Val Phe Ser Cys Ser Val Met His Glu
            420                 425                 430 gct ctg cac aac cac tac acg cag aag agc ctc tcc ctg tct ccg ggt         1344
Ala Leu His Asn His Tyr Thr Gln Lys Ser Leu Ser Leu Ser Pro Gly
                435                 440                 445 aaa tga                                                                 1350
Lys <210> SEQ ID NO 6
<211> LENGTH: 449
<212> TYPE: PRT
<213> ORGANISM: Artificial Sequence
<220> FEATURE:
<223> OTHER INFORMATION: Synthetic Construct

<400> SEQUENCE: 6

Gln Val Gln Met Gln Glu Ser Gly Pro Gly Leu Val Arg Pro Ser Gln
1               5                   10                  15

Thr Leu Ser Leu Thr Cys Thr Val Ser Gly Phe Ser Leu Ser Ser Tyr
            20                  25                  30

Ser Val His Trp Val Arg Gln Pro Pro Gly Arg Gly Leu Glu Trp Ile
        35                  40                  45

Gly Gly Ile Trp Ser Gly Gly Ser Ile His Tyr Thr Pro Ala Leu Ser
    50                  55                  60

Ser Arg Val Thr Val Leu Arg Asp Thr Ser Lys Asn Gln Val Ser Leu
65                  70                  75                  80

Arg Leu Ser Ser Val Thr Ala Ala Asp Thr Ala Val Tyr Tyr Cys Ala
                85                  90                  95

Arg Tyr Asp Arg Tyr Glu Thr Tyr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Trp Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 7
<211> LENGTH: 657
<212> TYPE: DNA
<213> ORGANISM: Artificial Sequence
<220> FEATURE:
<223> OTHER INFORMATION: L-chain of anti-human Ig-beta antibody
<220> FEATURE:
<221> NAME/KEY: CDS
<222> LOCATION: (1)..(657)

<400> SEQUENCE: 7 gac atc cag ctg acc cag tcc ccc tcc agc ctg tcc gcc tct gtg ggc      48
Asp Ile Gln Leu Thr Gln Ser Pro Ser Ser Leu Ser Ala Ser Val Gly
1               5                  10                  15 gac aga gtg acc atc aca tgc aag gcc tcc cag tcc gtg gac tac gac      96
Asp Arg Val Thr Ile Thr Cys Lys Ala Ser Gln Ser Val Asp Tyr Asp
                20                  25                  30 ggc gac tcc tac atg aac tgg tat cag cag aag ccc ggc aag gcc ccc     144
Gly Asp Ser Tyr Met Asn Trp Tyr Gln Gln Lys Pro Gly Lys Ala Pro
            35                  40                  45
```

```
aag ctg ctg atc tac gcc gcc tcc aac ctg gaa tcc ggc gtg ccc tcc    192
Lys Leu Leu Ile Tyr Ala Ala Ser Asn Leu Glu Ser Gly Val Pro Ser
     50                  55                  60 aga ttc tcc ggc tcc ggc tct ggc acc gac ttc acc ttc acc atc tcc    240
Arg Phe Ser Gly Ser Gly Ser Gly Thr Asp Phe Thr Phe Thr Ile Ser
 65                  70                  75                  80 agc ctg cag ccc gag gat atc gcc acc tac tac tgc cag cag tcc aac    288
Ser Leu Gln Pro Glu Asp Ile Ala Thr Tyr Tyr Cys Gln Gln Ser Asn
                 85                  90                  95 gag gac ccc ctg acc ttc ggc cag ggc acc aag gtg gaa atc aag cgt    336
Glu Asp Pro Leu Thr Phe Gly Gln Gly Thr Lys Val Glu Ile Lys Arg
            100                 105                 110 acg gtg gct gca cca tct gtc ttc atc ttc ccg cca tct gat gag cag    384
Thr Val Ala Ala Pro Ser Val Phe Ile Phe Pro Pro Ser Asp Glu Gln
                115                 120                 125 ttg aaa tct gga act gcc tct gtt gtg tgc ctg ctg aat aac ttc tat    432
Leu Lys Ser Gly Thr Ala Ser Val Val Cys Leu Leu Asn Asn Phe Tyr
130                 135                 140 ccc aga gag gcc aaa gta cag tgg aag gtg gat aac gcc ctc caa tcg    480
Pro Arg Glu Ala Lys Val Gln Trp Lys Val Asp Asn Ala Leu Gln Ser
145                 150                 155                 160 ggt aac tcc cag gag agt gtc aca gag cag gac agc aag gac agc acc    528
Gly Asn Ser Gln Glu Ser Val Thr Glu Gln Asp Ser Lys Asp Ser Thr
                165                 170                 175 tac agc ctc agc agc acc ctg acg ctg agc aaa gca gac tac gag aaa    576
Tyr Ser Leu Ser Ser Thr Leu Thr Leu Ser Lys Ala Asp Tyr Glu Lys
            180                 185                 190 cac aaa gtc tac gcc tgc gaa gtc acc cat cag ggc ctg agc tcg ccc    624
His Lys Val Tyr Ala Cys Glu Val Thr His Gln Gly Leu Ser Ser Pro
        195                 200                 205 gtc aca aag agc ttc aac agg gga gag tgt tag                        657
Val Thr Lys Ser Phe Asn Arg Gly Glu Cys
            210                 215

<210> SEQ ID NO 8
<211> LENGTH: 218
<212> TYPE: PRT
<213> ORGANISM: Artificial Sequence
<220> FEATURE:
<223> OTHER INFORMATION: Synthetic Construct

<400> SEQUENCE: 8

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
     50                  55                  60

Arg Phe Ser Gly Ser Gly Ser Gly Thr Asp Phe Thr Phe Thr Ile Ser
 65                  70                  75                  80

Ser Leu Gln Pro Glu Asp Ile Ala Thr Tyr Tyr Cys Gln Gln Ser Asn
                 85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
```

```
                                 130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 9
<211> LENGTH: 1350
<212> TYPE: DNA
<213> ORGANISM: Artificial Sequence
<220> FEATURE:
<223> OTHER INFORMATION: H-chain of anti-human Ig-beta antibody
<220> FEATURE:
<221> NAME/KEY: CDS
<222> LOCATION: (1)..(1350)

<400> SEQUENCE: 9 gaa gtg cag ctg gtg gag tcc ggg gga ggt ctg gtg cag ccc ggg ggt       48
Glu Val Gln Leu Val Glu Ser Gly Gly Gly Leu Val Gln Pro Gly Gly
1               5                   10                  15 tct ctg cgt ctg tct tgt gcc gtg tct ggg ttt agt ctg tcc agc tat       96
Ser Leu Arg Leu Ser Cys Ala Val Ser Gly Phe Ser Leu Ser Ser Tyr
            20                  25                  30 agt gtg cac tgg ttc cga aag gct ccc ggc aaa gga ctg gag tgg ctg      144
Ser Val His Trp Phe Arg Lys Ala Pro Gly Lys Gly Leu Glu Trp Leu
        35                  40                  45 ggc gga atc tgg tca ggg ggt tcc att cat tat acc cct gca ctg tct      192
Gly Gly Ile Trp Ser Gly Gly Ser Ile His Tyr Thr Pro Ala Leu Ser
    50                  55                  60 agt aga ctg aca gtg agc cgc gac atc tct aag aac aca gtc tac ctg      240
Ser Arg Leu Thr Val Ser Arg Asp Ile Ser Lys Asn Thr Val Tyr Leu
65                  70                  75                  80 cag atg aat agc ctg agg gcc gag gat acc gct gtc tac tat tgc gca      288
Gln Met Asn Ser Leu Arg Ala Glu Asp Thr Ala Val Tyr Tyr Cys Ala
                85                  90                  95 aga tac gac cgg tat gaa act tac gcc atg gat tac tgg ggc cag ggc      336
Arg Tyr Asp Arg Tyr Glu Thr Tyr Ala Met Asp Tyr Trp Gly Gln Gly
            100                 105                 110 acc ctg gtc acc gtc tcc tca gcc tcc acc aag ggc cca tcg gtc ttc      384
Thr Leu Val Thr Val Ser Ser Ala Ser Thr Lys Gly Pro Ser Val Phe
        115                 120                 125 ccc ctg gca ccc tcc tcc aag agc acc tct ggg ggc aca gcg gcc ctg      432
Pro Leu Ala Pro Ser Ser Lys Ser Thr Ser Gly Gly Thr Ala Ala Leu
    130                 135                 140 ggc tgc ctg gtc aag gac tac ttc ccc gaa ccg gtg acg gtg tcg tgg      480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta      528
Asn Ser Gly Ala Leu Thr Ser Gly Val His Thr Phe Pro Ala Val Leu
                165                 170                 175 cag tcc tca gga ctc tac tcc ctt agt agc gtg gtg acc gtg ccc tcc      576
Gln Ser Ser Gly Leu Tyr Ser Leu Ser Ser Val Val Thr Val Pro Ser
            180                 185                 190 agc agc ttg ggc acc cag acc tac atc tgc aac gtg aat cac aag ccc      624
```

```
Ser Ser Leu Gly Thr Gln Thr Tyr Ile Cys Asn Val Asn His Lys Pro
            195                 200                 205 agc aac acc aag gtg gac aag aaa gtt gag ccc aaa tct tgt gac aaa         672
Ser Asn Thr Lys Val Asp Lys Lys Val Glu Pro Lys Ser Cys Asp Lys
210                 215                 220 act cac aca tgc cca ccg tgc cca gca cct gaa ctc ctg ggg gga ccg         720
Thr His Thr Cys Pro Pro Cys Pro Ala Pro Glu Leu Leu Gly Gly Pro
225                 230                 235                 240 gac gtc ttc ctc ttc ccc cca aaa ccc aag gac acc ctc atg atc tcc         768
Asp Val Phe Leu Phe Pro Pro Lys Pro Lys Asp Thr Leu Met Ile Ser
                245                 250                 255 cgg acc cct gag gtc aca tgc gtg gtg gtg gac gtg agc gac gaa gac         816
Arg Thr Pro Glu Val Thr Cys Val Val Val Asp Val Ser Asp Glu Asp
            260                 265                 270 cct gag gtc aag ttc aac tgg tac gtg gac ggc gtg gag gtg cat aat         864
Pro Glu Val Lys Phe Asn Trp Tyr Val Asp Gly Val Glu Val His Asn
        275                 280                 285 gcc aag aca aag ccg cgg gag gag cag tac aac agc acg tac cgt gtg         912
Ala Lys Thr Lys Pro Arg Glu Glu Gln Tyr Asn Ser Thr Tyr Arg Val
290                 295                 300 gtc agc gtc ctc acc gtc ctg cac cag gac tgg ctg aat ggc aag gag         960
Val Ser Val Leu Thr Val Leu His Gln Asp Trp Leu Asn Gly Lys Glu
305                 310                 315                 320 tac aag tgc aag gtc tcc aac aaa gcc tgg cca gcc ccc atc gag aaa        1008
Tyr Lys Cys Lys Val Ser Asn Lys Ala Trp Pro Ala Pro Ile Glu Lys
                325                 330                 335 acc atc tcc aaa gcc aaa ggg cag ccc cga gaa cca cag gtg tac acc        1056
Thr Ile Ser Lys Ala Lys Gly Gln Pro Arg Glu Pro Gln Val Tyr Thr
            340                 345                 350 ctg ccc cca tcc cgg gat gag ctg acc aag aac cag gtc agc ctg acc        1104
Leu Pro Pro Ser Arg Asp Glu Leu Thr Lys Asn Gln Val Ser Leu Thr
        355                 360                 365 tgc ctg gtc aaa ggc ttc tat ccc agc gac atc gcc gtg gag tgg gag        1152
Cys Leu Val Lys Gly Phe Tyr Pro Ser Asp Ile Ala Val Glu Trp Glu
370                 375                 380 agc aat ggg cag ccg gag aac aac tac aag acc acg cct ccc gtg ctg        1200
Ser Asn Gly Gln Pro Glu Asn Asn Tyr Lys Thr Thr Pro Pro Val Leu
385                 390                 395                 400 gac tcc gac ggc tcc ttc ttc ctc tac agc aag ctc acc gtg gac aag        1248
Asp Ser Asp Gly Ser Phe Phe Leu Tyr Ser Lys Leu Thr Val Asp Lys
                405                 410                 415 agc agg tgg cag cag ggg aac gtc ttc tca tgc tcc gtg atg cat gag        1296
Ser Arg Trp Gln Gln Gly Asn Val Phe Ser Cys Ser Val Met His Glu
            420                 425                 430 gct ctg cac aac cac tac acg cag aag agc ctc tcc ctg tct ccg ggt        1344
Ala Leu His Asn His Tyr Thr Gln Lys Ser Leu Ser Leu Ser Pro Gly
        435                 440                 445 aaa tga                                                                1350
Lys

<210> SEQ ID NO 10
<211> LENGTH: 449
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15
```

```
Ser Leu Arg Leu Ser Cys Ala Val Ser Gly Phe Ser Leu Ser Ser Tyr
            20                  25                  30

Ser Val His Trp Phe Arg Lys Ala Pro Gly Lys Gly Leu Glu Trp Leu
            35                  40                  45

Gly Gly Ile Trp Ser Gly Gly Ser Ile His Tyr Thr Pro Ala Leu Ser
        50                  55                  60

Ser Arg Leu Thr Val Ser Arg Asp Ile Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Tyr Asp Arg Tyr Glu Thr Tyr Ala Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Trp Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

```
                  435                 440                 445
Lys

<210> SEQ ID NO 11
<211> LENGTH: 657
<212> TYPE: DNA
<213> ORGANISM: Artificial Sequence
<220> FEATURE:
<223> OTHER INFORMATION: L-chain of anti-human Ig-beta antibody
<220> FEATURE:
<221> NAME/KEY: CDS
<222> LOCATION: (1)..(657)

<400> SEQUENCE: 11 gac atc gtg ctg acc cag tcc ccc tcc agc ctg tcc gcc tct gtg ggc      48
Asp Ile Val Leu Thr Gln Ser Pro Ser Ser Leu Ser Ala Ser Val Gly
1               5                   10                  15 gac aga gtg acc atc aca tgc aag gcc tcc cag tcc gtg gac tac gac      96
Asp Arg Val Thr Ile Thr Cys Lys Ala Ser Gln Ser Val Asp Tyr Asp
            20                  25                  30 ggc gac tcc tac atg aac tgg tat cag cag aag ccc ggc aag gcc ccc     144
Gly Asp Ser Tyr Met Asn Trp Tyr Gln Gln Lys Pro Gly Lys Ala Pro
        35                  40                  45 aag ctg ctg atc tac gcc gcc tcc aac ctg gaa tcc ggc gtg ccc tcc     192
Lys Leu Leu Ile Tyr Ala Ala Ser Asn Leu Glu Ser Gly Val Pro Ser
    50                  55                  60 aga ttc tcc ggc tcc ggc tct ggc acc gac ttc acc ctg acc atc tcc     240
Arg Phe Ser Gly Ser Gly Ser Gly Thr Asp Phe Thr Leu Thr Ile Ser
65                  70                  75                  80 agc ctg cag ccc gag gac ttc gcc acc tac tac tgc cag cag tcc aac     288
Ser Leu Gln Pro Glu Asp Phe Ala Thr Tyr Tyr Cys Gln Gln Ser Asn
                85                  90                  95 gag gac ccc ctg acc ttc ggc cag ggc acc aag gtg gaa atc aag cgt     336
Glu Asp Pro Leu Thr Phe Gly Gln Gly Thr Lys Val Glu Ile Lys Arg
            100                 105                 110 acg gtg gct gca cca tct gtc ttc atc ttc ccg cca tct gat gag cag     384
Thr Val Ala Ala Pro Ser Val Phe Ile Phe Pro Pro Ser Asp Glu Gln
        115                 120                 125 ttg aaa tct gga act gcc tct gtt gtg tgc ctg ctg aat aac ttc tat     432
Leu Lys Ser Gly Thr Ala Ser Val Val Cys Leu Leu Asn Asn Phe Tyr
    130                 135                 140 ccc aga gag gcc aaa gta cag tgg aag gtg gat aac gcc ctc caa tcg     480
Pro Arg Glu Ala Lys Val Gln Trp Lys Val Asp Asn Ala Leu Gln Ser
145                 150                 155                 160 ggt aac tcc cag gag agt gtc aca gag cag gac agc aag gac agc acc     528
Gly Asn Ser Gln Glu Ser Val Thr Glu Gln Asp Ser Lys Asp Ser Thr
                165                 170                 175 tac agc ctc agc agc acc ctg acg ctg agc aaa gca gac tac gag aaa     576
Tyr Ser Leu Ser Ser Thr Leu Thr Leu Ser Lys Ala Asp Tyr Glu Lys
            180                 185                 190 cac aaa gtc tac gcc tgc gaa gtc acc cat cag ggc ctg agc tcg ccc     624
His Lys Val Tyr Ala Cys Glu Val Thr His Gln Gly Leu Ser Ser Pro
        195                 200                 205 gtc aca aag agc ttc aac agg gga gag tgt tag                         657
Val Thr Lys Ser Phe Asn Arg Gly Glu Cys
    210                 215

<210> SEQ ID NO 12
<211> LENGTH: 218
<212> TYPE: PRT
<213> ORGANISM: Artificial Sequence
<220> FEATURE:
```

<223> OTHER INFORMATION: Synthetic Construct

<400> SEQUENCE: 12

Asp Ile Val Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 13
<211> LENGTH: 450
<212> TYPE: DNA
<213> ORGANISM: Artificial Sequence
<220> FEATURE:
<223> OTHER INFORMATION: Human Ig-beta-Flag fusion gene
<220> FEATURE:
<221> NAME/KEY: CDS
<222> LOCATION: (1)..(447)

<400> SEQUENCE: 13 gcc aga tcg gag gac cgg tac cgg aat ccc aaa ggt agt gct tgt tcg      48
Ala Arg Ser Glu Asp Arg Tyr Arg Asn Pro Lys Gly Ser Ala Cys Ser
1               5                   10                  15 cgg atc tgg cag agc cca cgt ttc ata gcc agg aaa cgg ggc ttc acg      96
Arg Ile Trp Gln Ser Pro Arg Phe Ile Ala Arg Lys Arg Gly Phe Thr
            20                  25                  30 gtg aaa atg cac tgc tac atg aac agc gcc tcc ggc aat gtg agc tgg     144
Val Lys Met His Cys Tyr Met Asn Ser Ala Ser Gly Asn Val Ser Trp
        35                  40                  45 ctc tgg aag cag gag atg gac gag aat ccc cag cag ctg aag ctg gaa     192
Leu Trp Lys Gln Glu Met Asp Glu Asn Pro Gln Gln Leu Lys Leu Glu
    50                  55                  60 aag ggc cgc atg gaa gag tcc cag aac gaa tct ctc gcc acc ctc acc     240
Lys Gly Arg Met Glu Glu Ser Gln Asn Glu Ser Leu Ala Thr Leu Thr
65                  70                  75                  80

```
atc caa ggc atc cgg ttt gag gac aat ggc atc tac ttc tgt cag cag      288
Ile Gln Gly Ile Arg Phe Glu Asp Asn Gly Ile Tyr Phe Cys Gln Gln
                85                  90                  95 aag tgc aac aac acc tcg gag gtc tac cag ggc tgc ggc aca gag ctg      336
Lys Cys Asn Asn Thr Ser Glu Val Tyr Gln Gly Cys Gly Thr Glu Leu
            100                 105                 110 cga gtc atg gga ttc agc acc ttg gca cag ctg aag cag agg aac acg      384
Arg Val Met Gly Phe Ser Thr Leu Ala Gln Leu Lys Gln Arg Asn Thr
        115                 120                 125 ctg aag gat tcg tca gca gac ctg gtt ccg cgc gga tcc gac tac aag      432
Leu Lys Asp Ser Ser Ala Asp Leu Val Pro Arg Gly Ser Asp Tyr Lys
    130                 135                 140 gac gat gac gat aaa tga                                              450
Asp Asp Asp Asp Lys
145

<210> SEQ ID NO 14
<211> LENGTH: 453
<212> TYPE: DNA
<213> ORGANISM: Artificial Sequence
<220> FEATURE:
<223> OTHER INFORMATION: Monkey Ig-beta-Flag fusion gene
<220> FEATURE:
<221> NAME/KEY: CDS
<222> LOCATION: (1)..(450)

<400> SEQUENCE: 14 gcc aaa tca gag gac ctg tac ccg aat ccc aaa ggt agt gct tgt tct       48
Ala Lys Ser Glu Asp Leu Tyr Pro Asn Pro Lys Gly Ser Ala Cys Ser
1               5                   10                  15 cgg atc tgg cag agc cca cgt ttc ata gcc agg aaa cgg ggc ttc acg       96
Arg Ile Trp Gln Ser Pro Arg Phe Ile Ala Arg Lys Arg Gly Phe Thr
            20                  25                  30 gtg aaa atg cac tgc tac gtg acc aac agc acc ttc agc atc gtg agc      144
Val Lys Met His Cys Tyr Val Thr Asn Ser Thr Phe Ser Ile Val Ser
        35                  40                  45 tgg ctc cgg aag cgg gag acg gac aag gag ccc caa cag gtg aac ctg      192
Trp Leu Arg Lys Arg Glu Thr Asp Lys Glu Pro Gln Gln Val Asn Leu
    50                  55                  60 gag cag ggc cac atg cat cag acc caa aac agc tct gtc acc acc ctc      240
Glu Gln Gly His Met His Gln Thr Gln Asn Ser Ser Val Thr Thr Leu
65                  70                  75                  80 atc atc caa gac atc cgg ttt gag gac aac ggc atc tac ttc tgt cag      288
Ile Ile Gln Asp Ile Arg Phe Glu Asp Asn Gly Ile Tyr Phe Cys Gln
                85                  90                  95 cag gag tgc agc aag acc tcg gag gtc tac cgg ggc tgc ggc acg gag      336
Gln Glu Cys Ser Lys Thr Ser Glu Val Tyr Arg Gly Cys Gly Thr Glu
            100                 105                 110 ctg cga gtc atg ggg ttc agc acc ttg gca cag ctg aag cag agg aac      384
Leu Arg Val Met Gly Phe Ser Thr Leu Ala Gln Leu Lys Gln Arg Asn
        115                 120                 125 acg ctg aag gat tcg tca gca gac ctg gtt ccg cgc gga tcc gac tac      432
Thr Leu Lys Asp Ser Ser Ala Asp Leu Val Pro Arg Gly Ser Asp Tyr
    130                 135                 140 aag gac gat gac gat aaa tga                                          453
Lys Asp Asp Asp Asp Lys
145                 150

<210> SEQ ID NO 15
<211> LENGTH: 1350
<212> TYPE: DNA
<213> ORGANISM: Artificial Sequence
<220> FEATURE:
```

<223> OTHER INFORMATION: H-chain of anti-human Ig-beta antibody
<220> FEATURE:
<221> NAME/KEY: CDS
<222> LOCATION: (1)..(1350)

<400> SEQUENCE: 15

| | | | | | | | | | | | | | | | | |
|---|---|---|---|---|---|---|---|---|---|---|---|---|---|---|---|---|
| gag | gtg | cag | atg | gtg | gaa | tcc | ggc | gga | ggc | ctg | gtg | cag | cct | ggc | ggc | 48 |
| Glu | Val | Gln | Met | Val | Glu | Ser | Gly | Gly | Gly | Leu | Val | Gln | Pro | Gly | Gly | |
| 1 | | | | 5 | | | | | 10 | | | | | 15 | | |
| tct | ctg | aga | ctg | tcc | tgc | gcc | gtg | tcc | ggc | ttc | agc | ctg | tcc | tcc | tac | 96 |
| Ser | Leu | Arg | Leu | Ser | Cys | Ala | Val | Ser | Gly | Phe | Ser | Leu | Ser | Ser | Tyr | |
| | | | 20 | | | | | 25 | | | | | 30 | | | |
| tcc | gtg | cac | tgg | gtc | cga | cag | gcc | cct | ggc | aag | gga | ctg | gaa | tgg | gtg | 144 |
| Ser | Val | His | Trp | Val | Arg | Gln | Ala | Pro | Gly | Lys | Gly | Leu | Glu | Trp | Val | |
| | | 35 | | | | | 40 | | | | | 45 | | | | |
| gcc | ggc | att | tgg | agc | ggc | ggc | tcc | atc | cac | tac | acc | cct | gcc | ctg | tcc | 192 |
| Ala | Gly | Ile | Trp | Ser | Gly | Gly | Ser | Ile | His | Tyr | Thr | Pro | Ala | Leu | Ser | |
| | 50 | | | | | 55 | | | | | 60 | | | | | |
| tcc | cgg | ttc | acc | gtg | tcc | cgg | gac | gac | tcc | aag | aac | acc | gtg | tac | ctg | 240 |
| Ser | Arg | Phe | Thr | Val | Ser | Arg | Asp | Asp | Ser | Lys | Asn | Thr | Val | Tyr | Leu | |
| 65 | | | | | 70 | | | | | 75 | | | | | 80 | |
| cag | atg | aac | tcc | ctg | cgg | gcc | gag | gac | acc | gcc | gtg | tac | tac | tgc | gcc | 288 |
| Gln | Met | Asn | Ser | Leu | Arg | Ala | Glu | Asp | Thr | Ala | Val | Tyr | Tyr | Cys | Ala | |
| | | | | 85 | | | | | 90 | | | | | 95 | | |
| cgc | tac | gac | aga | tac | gag | aca | tac | gcc | atg | gac | tac | tgg | ggc | cag | ggc | 336 |
| Arg | Tyr | Asp | Arg | Tyr | Glu | Thr | Tyr | Ala | Met | Asp | Tyr | Trp | Gly | Gln | Gly | |
| | | | 100 | | | | | 105 | | | | | 110 | | | |
| acc | ctg | gtg | aca | gtg | tcc | tcc | gcc | tcc | acc | aag | ggc | ccc | tcc | gtg | ttc | 384 |
| Thr | Leu | Val | Thr | Val | Ser | Ser | Ala | Ser | Thr | Lys | Gly | Pro | Ser | Val | Phe | |
| | | 115 | | | | | 120 | | | | | 125 | | | | |
| cct | ctg | gcc | ccc | tcc | agc | aag | tcc | acc | tct | ggc | ggc | acc | gct | gcc | ctg | 432 |
| Pro | Leu | Ala | Pro | Ser | Ser | Lys | Ser | Thr | Ser | Gly | Gly | Thr | Ala | Ala | Leu | |
| | 130 | | | | | 135 | | | | | 140 | | | | | |
| ggc | tgc | ctg | gtg | aaa | gac | tac | ttc | ccc | gag | ccc | gtg | acc | gtg | tcc | tgg | 480 |
| Gly | Cys | Leu | Val | Lys | Asp | Tyr | Phe | Pro | Glu | Pro | Val | Thr | Val | Ser | Trp | |
| 145 | | | | | 150 | | | | | 155 | | | | | 160 | |
| aac | tct | ggc | gcc | ctg | acc | tcc | ggc | gtg | cac | acc | ttc | cct | gcc | gtg | ctg | 528 |
| Asn | Ser | Gly | Ala | Leu | Thr | Ser | Gly | Val | His | Thr | Phe | Pro | Ala | Val | Leu | |
| | | | | 165 | | | | | 170 | | | | | 175 | | |
| cag | tcc | tcc | ggc | ctg | tac | tcc | ctg | tcc | agc | gtg | gtg | acc | gtg | ccc | tcc | 576 |
| Gln | Ser | Ser | Gly | Leu | Tyr | Ser | Leu | Ser | Ser | Val | Val | Thr | Val | Pro | Ser | |
| | | | 180 | | | | | 185 | | | | | 190 | | | |
| agc | tct | ctg | ggc | acc | cag | acc | tac | atc | tgc | aac | gtg | aac | cac | aag | ccc | 624 |
| Ser | Ser | Leu | Gly | Thr | Gln | Thr | Tyr | Ile | Cys | Asn | Val | Asn | His | Lys | Pro | |
| | | 195 | | | | | 200 | | | | | 205 | | | | |
| tcc | aac | acc | aag | gtg | gac | aag | aag | gtg | gaa | ccc | aag | tcc | tgc | gac | aag | 672 |
| Ser | Asn | Thr | Lys | Val | Asp | Lys | Lys | Val | Glu | Pro | Lys | Ser | Cys | Asp | Lys | |
| | 210 | | | | | 215 | | | | | 220 | | | | | |
| acc | cac | acc | tgt | ccc | cct | tgc | cct | gcc | cct | gag | ctg | ctg | ggc | gga | ccc | 720 |
| Thr | His | Thr | Cys | Pro | Pro | Cys | Pro | Ala | Pro | Glu | Leu | Leu | Gly | Gly | Pro | |
| 225 | | | | | 230 | | | | | 235 | | | | | 240 | |
| gat | gtg | ttt | ctg | ttc | ccc | cca | aag | ccc | aag | gac | acc | ctg | atg | atc | tcc | 768 |
| Asp | Val | Phe | Leu | Phe | Pro | Pro | Lys | Pro | Lys | Asp | Thr | Leu | Met | Ile | Ser | |
| | | | | 245 | | | | | 250 | | | | | 255 | | |
| cgg | acc | ccc | gaa | gtg | acc | tgc | gtg | gtg | gtg | gac | gtg | tcc | gac | gag | gac | 816 |
| Arg | Thr | Pro | Glu | Val | Thr | Cys | Val | Val | Val | Asp | Val | Ser | Asp | Glu | Asp | |
| | | | 260 | | | | | 265 | | | | | 270 | | | |
| cct | gaa | gtg | aag | ttc | aat | tgg | tac | gtg | gac | ggc | gtg | gaa | gtg | cac | aac | 864 |
| Pro | Glu | Val | Lys | Phe | Asn | Trp | Tyr | Val | Asp | Gly | Val | Glu | Val | His | Asn | |
| | | 275 | | | | | 280 | | | | | 285 | | | | |

| | | | | |
|---|---|---|---|---|
| gcc aag acc aag ccc aga gag gaa cag tac aac tcc acc tac cgg gtg | | | | 912 |
| Ala Lys Thr Lys Pro Arg Glu Glu Gln Tyr Asn Ser Thr Tyr Arg Val | | | | |
| 290 295 300 | | | | |
| gtg tcc gtg ctg acc gtg ctg cac cag gac tgg ctg aac ggc aaa gaa | | | | 960 |
| Val Ser Val Leu Thr Val Leu His Gln Asp Trp Leu Asn Gly Lys Glu | | | | |
| 305 310 315 320 | | | | |
| tac aag tgc aag gtt tcc aac aag gcc tgg cct gcc ccc atc gaa aag | | | | 1008 |
| Tyr Lys Cys Lys Val Ser Asn Lys Ala Trp Pro Ala Pro Ile Glu Lys | | | | |
| 325 330 335 | | | | |
| acc atc tcc aag gcc aag ggc cag ccc cgc gag ccc cag gtg tac acc | | | | 1056 |
| Thr Ile Ser Lys Ala Lys Gly Gln Pro Arg Glu Pro Gln Val Tyr Thr | | | | |
| 340 345 350 | | | | |
| ctg ccc cct agc cgg gac gag ctg acc aag aac cag gtg tcc ctg acc | | | | 1104 |
| Leu Pro Pro Ser Arg Asp Glu Leu Thr Lys Asn Gln Val Ser Leu Thr | | | | |
| 355 360 365 | | | | |
| tgt ctg gtg aaa ggc ttc tac ccc tcc gat atc gcc gtg gaa tgg gag | | | | 1152 |
| Cys Leu Val Lys Gly Phe Tyr Pro Ser Asp Ile Ala Val Glu Trp Glu | | | | |
| 370 375 380 | | | | |
| tcc aac ggc cag ccc gag aac aac tac aag acc acc ccc cct gtg ctg | | | | 1200 |
| Ser Asn Gly Gln Pro Glu Asn Asn Tyr Lys Thr Thr Pro Pro Val Leu | | | | |
| 385 390 395 400 | | | | |
| gac tcc gac ggc tca ttc ttc ctg tac tcc aag ctg acc gtg gac aag | | | | 1248 |
| Asp Ser Asp Gly Ser Phe Phe Leu Tyr Ser Lys Leu Thr Val Asp Lys | | | | |
| 405 410 415 | | | | |
| tcc cgg tgg cag cag ggc aac gtg ttc tcc tgc tcc gtg atg cac gag | | | | 1296 |
| Ser Arg Trp Gln Gln Gly Asn Val Phe Ser Cys Ser Val Met His Glu | | | | |
| 420 425 430 | | | | |
| gcc ctg cac aat cac tac acc cag aag tcc ctg tcc ctg agc ccc ggc | | | | 1344 |
| Ala Leu His Asn His Tyr Thr Gln Lys Ser Leu Ser Leu Ser Pro Gly | | | | |
| 435 440 445 | | | | |
| aag tga | | | | 1350 |
| Lys | | | | |